United States Patent
Borthwick et al.

(10) Patent No.: US 7,329,685 B2
(45) Date of Patent: Feb. 12, 2008

(54) 1-PHENYL-2-OXO-3-SULFONYLAMINO-PYRROLIDINE DERIVATIVES AND RELATED COMPOUNDS AS FACTOR XA INHIBITORS FOR THE TREATMENT OF ACUTE VASCULAR DISEASES

(75) Inventors: Alan David Borthwick, Stevenage (GB); Chuen Chan, Stevenage (GB); Henry Anderson Kelly, Stevenage (GB); Savvas Kleanthous, Stevenage (GB); Andrew McMurtrie Mason, Stevenage (GB); Nigel Stephen Watson, Stevenage (GB)

(73) Assignee: Glaxo Group Limited, Greenford, Middlesex (GB)

( * ) Notice: Subject to any disclaimer, the term of this patent is extended or adjusted under 35 U.S.C. 154(b) by 53 days.

(21) Appl. No.: 10/561,545

(22) PCT Filed: Jun. 17, 2004

(86) PCT No.: PCT/EP2004/006592

§ 371 (c)(1),
(2), (4) Date: Dec. 19, 2005

(87) PCT Pub. No.: WO2004/110435

PCT Pub. Date: Dec. 23, 2004

(65) Prior Publication Data

US 2006/0148879 A1    Jul. 6, 2006

(30) Foreign Application Priority Data

Jun. 19, 2003   (GB) ................... 0314299.9

(51) Int. Cl.
*A61K 31/40* (2006.01)
*C07D 207/40* (2006.01)

(52) U.S. Cl. .............. 514/422; 514/424; 514/426; 548/545; 548/546; 548/557

(58) Field of Classification Search ............... 514/422, 514/424, 426; 548/545, 546, 557
See application file for complete search history.

(56) References Cited

U.S. PATENT DOCUMENTS

| | | | |
|---|---|---|---|
| 6,034,093 A | 3/2000 | Ewing et al. | |
| 6,348,600 B1 | 2/2002 | Ono et al. | |
| 7,157,470 B2 * | 1/2007 | Smallheer et al. | 514/318 |
| 2002/0183324 A1 | 12/2002 | Jacobson et al. | |

FOREIGN PATENT DOCUMENTS

| | | |
|---|---|---|
| WO | 92/10476 | 6/1992 |
| WO | 97/43257 | 11/1997 |
| WO | 2002/002519 | 1/2002 |
| WO | 2002/080853 | 10/2002 |
| WO | 03/043981 | 5/2003 |
| WO | WO 2003043981 A1 * | 5/2003 |
| WO | 03/053925 | 7/2003 |

* cited by examiner

*Primary Examiner*—Rebecca Anderson
*Assistant Examiner*—Susannah Chung
(74) *Attorney, Agent, or Firm*—Jennifer L. Fox

(57) ABSTRACT

The invention relates to compounds of formula (I):

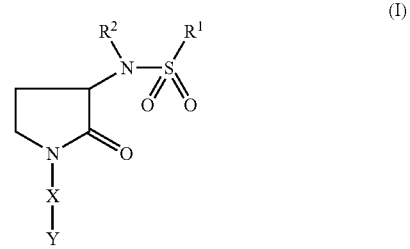

wherein substituents are as defined.

8 Claims, No Drawings

1-PHENYL-2-OXO-3-SULFONYLAMINO-PYRROLIDINE DERIVATIVES AND RELATED COMPOUNDS AS FACTOR XA INHIBITORS FOR THE TREATMENT OF ACUTE VASCULAR DISEASES

This application is filed pursuant to 35 U.S.C. § 371 as a United States National Phase Application of International Application No. PCT/EP2004/006592 filed Jun. 17, 2004, which claims priority from GB 0314299.9 filed Jun. 19, 2003.

FIELD OF THE INVENTION

The present invention relates to a novel class of chemical compounds, to processes for their preparation, to pharmaceutical compositions containing them and to their use in medicine, particularly use in the amelioration of a clinical condition for which a Factor Xa Inhibitor is indicated.

BACKGROUND OF THE INVENTION

Factor Xa is a member of the trypsin-like serine protease class of enzymes. It is a key enzyme in the coagulation cascade. A one-to-one binding of Factors Xa and Va with calcium ions and phospholipid converts prothrombin into thrombin. Thrombin plays a central role in the mechanism of blood coagulation by converting the soluble plasma protein, fibrinogen, into insoluble fibrin. The insoluble fibrin matrix is required for the stabilisation of the primary hemostatic plug. Many significant disease states are related to abnormal hemostasis. With respect to the coronary arterial vasculature, abnormal thrombus formation due to the rupture of an established atherosclerotic plaque is the major cause of acute myocardial infarction and unstable angina. Both treatment of an occlusive coronary thrombus by thrombolytic therapy and percutaneous transluminal coronary angioplasty (PTCA) are often accompanied by an acute thrombotic reclosure of the affected vessel which requires immediate resolution. With respect to the venous vasculature, a high percentage of patients undergoing major surgery in the lower extremities or the abdominal area suffer from thrombus formation in the venous vasculature which can result in reduced blood flow to the affected extremity and a predisposition to pulmonary embolism. Disseminated intravascular coagulopathy commonly occurs within both vascular systems during septic shock, certain viral infections and cancer and is characterised by the rapid consumption of coagulation factors and systemic coagulation which results in the formation of life-threatening thrombi occurring throughout the vasculature leading to widespread organ failure. Beyond its direct role in the formation of fibrin rich blood clots, thrombin has been reported to have profound bioregulatory effects on a number of cellular components within the vasculature and blood, (Shuman, M. A., Ann. N Y Acad. Sci., 405: 349 (1986)).

A Factor Xa Inhibitor may be useful In the treatment of acute vascular diseases such as acute coronary syndromes (for example primary and secondary prevention of myocardial infarction and unstable angina and treatment of prothrombotic sequalae associated with myocardial infarction or heart failure), thromboembolism, acute vessel closure associated with thrombolytic therapy and percutaneous transluminal coronary angioplasty, transient ischemic attacks, pulmonary embolism, deep vein thrombosis, peripheral arterial occlusion, prevention of vessel luminal narrowing (restenosis), and the prevention of thromboembolic events associated with atrial fibrillation, e.g. stroke. Factor Xa inhibitors may also be useful in preventing thrombosis and complications in patients genetically predisposed to arterial thrombosis or venous thrombosis and patients that have a disease-associated predisposition to thrombosis (e.g. type 2 diabetics). Thrombin has been reported to contribute to lung fibroblast proliferation, thus, Factor Xa inhibitors could be useful for the treatment of some pulmonary fibrotic diseases. Factor Xa inhibitors could also be useful in the treatment of tumour metastasis, by suppressing coagulation and thus preventing fibrin deposition and its concommittant facilitation of metastasis. A Factor Xa inhibitor may also have utility as an anti-inflammatory agent through its inhibition of FXa mediated activation of protease-activated receptors (PARs 1 and 2). A Factor Xa inhibitor may also have utility as an anti-atherosclerotic agent through the suppression of platelet-activation. Thrombin can induce neurite retraction and thus Factor Xa inhibitors may have potential in neurogenerative diseases such as Parkinson's and Alzheimer's disease. Factor Xa inhibitors may also have utility as anticoagulant agents in connection with the preparation, storage, fractionation or use of whole blood. They have also been reported for use in conjunction with thrombolytic agents, thus permitting the use of a lower dose of thrombolytic agent.

DESCRIPTION OF THE INVENTION

The present invention provides compounds of formula (I):

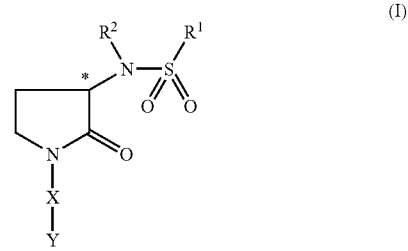

(I)

wherein:
$R^1$ represents a group selected from:

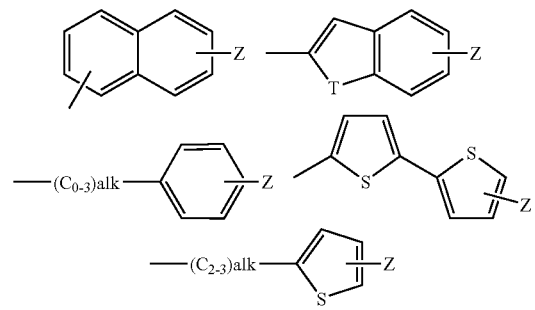

each ring of which optionally contains a further heteroatom N,
Z represents an optional substituent halogen,
alk represents alkylene or alkenylene,
T represents S, O or NH;
$R^2$ represents —$C_{1-6}$alkyl, —$C_{1-3}$alkylCN, —$C_{0-3}$alkyl$R^c$, —$C_{1-3}$alkyl$R^f$, —$C_{2-3}$alkylNR$^a$R$^b$, —$C_{2-3}$alkylO$C_{1-6}$ alkyl, —C$_{2-3}$alkylOC$_{1-3}$alkylCONR$^a$R$^b$, with the proviso that R$^2$ does not represent C$_{2-3}$alkylmorpholino;

R$^a$ and R$^b$ independently represent hydrogen, —C$_{1-6}$alkyl, or together with the N atom to which they are bonded form a 5-, 6- or 7-membered non-aromatic heterocyclic ring optionally containing an additional heteroatom selected from O, N or S, optionally substituted by —C$_{1-4}$alkyl, and optionally the S heteroatom is substituted by O i.e. represents S(O)$_n$;

R$_c$ represents —C$_{3-6}$cycloalkyl;

R$^f$ represents phenyl or a 5- or 6-membered aromatic heterocyclic ring, containing at least one heteroatom selected from O, N or S, optionally substituted by 0 to 2 groups selected from —C$_{1-4}$alkyl or —NH$_2$, and optionally the S or N heteroatom is substituted by O, i.e. represents S(O)$_n$ or N-oxide;

n represents 0-2;

X represents phenyl or a 5 or 6-membered aromatic heterocyclic group containing at least one heteroatom selected from O, N or S, each of which is optionally substituted by 0-2 groups selected from: halogen, —C$_{1-4}$alkyl, —C$_{2-4}$alkenyl, —CN, —CF$_3$, —NR$^a$R$^b$, —C$_{0-4}$alkylOR$^e$, —C(O)R$^d$ and —C(O)NR$^a$R$^b$;

R$^e$ represents hydrogen or —C$_{1-6}$alkyl;

Y represents a substituent selected from hydrogen, halogen, —C$_{1-4}$alkyl, —C$_{2-4}$alkenyl, —NR$^a$R$^b$, —NO$_2$, —C(O)NR$^a$R$^b$, —N(C$_{1-4}$alkyl)(CHO), —NHCOC$_{1-4}$alkyl, —NHSO$_2$R$^d$, —C$_{0-4}$alkylOR$^e$, —C(O)R$^d$, —S(O)$_n$R$^d$, or —S(O)$_2$NR$^a$R$^b$;

R$^d$ represents —C$_{1-6}$alkyl;

and/or pharmaceutically acceptable derivative thereof.

Further aspects of the invention are:

A pharmaceutical composition comprising a compound of the invention together with a pharmaceutical carrier and/or excipient.

A compound of the invention for use in therapy.

Use of a compound of the invention for the manufacture of a medicament for the treatment of a patient suffering from a condition susceptible to amelioration by a Factor Xa inhibitor.

A method of treating a patient suffering from a condition susceptible to amelioration by a Factor Xa inhibitor comprising administering a therapeutically effective amount of a compound of the invention.

In another aspect, the present invention provides compounds of formula (I):

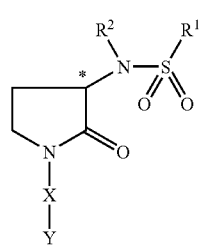

(I)

wherein:

R$^1$ represents a group selected from:

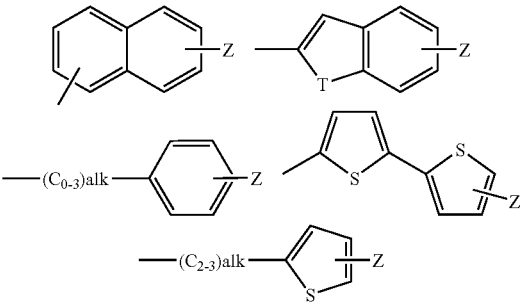

each ring of which optionally contains a further heteroatom N,

Z represents an optional substituent halogen, alk represents alkylene or alkenylene, T represents S, O or NH;

R$^2$ represents —C$_{1-6}$alkyl, —C$_{1-3}$alkylCN, —C$_{0-3}$alkylR$^c$, —C$_{1-3}$alkylR$^f$, —C$_{2-3}$alkylNR$^a$R$^b$, —C$_{1-3}$alkylOC$_{1-6}$alkyl, —C$_{2-3}$alkylOC$_{1-3}$alkylCONR$^a$R$^b$;

R$^a$ and R$^b$ independently represent hydrogen, —C$_{1-6}$alkyl, or together with the N atom to which they are bonded form a 5-, 6- or 7-membered non-aromatic heterocyclic ring optionally containing an additional heteroatom selected from O, N or S, optionally substituted by —C$_{1-4}$alkyl, and optionally the S heteroatom is substituted by O i.e. represents S(O)$_n$;

R$_c$ represents —C$_{3-6}$cycloalkyl;

R$^f$ represents phenyl or a 5- or 6-membered aromatic heterocyclic ring, containing at least one heteroatom selected from O, N or S, optionally substituted by 0 to 2 groups selected from —C$_{1-4}$alkyl or —NH$_2$, and optionally the S or N heteroatom is substituted by O, i.e. represents S(O)$_n$ or N-oxide;

X represents phenyl or a 5- or 6-membered aromatic heterocyclic group containing at least one heteroatom selected from O, N or S, each of which is optionally substituted by 0-2 groups selected from: halogen, —C$_{1-4}$alkyl, —C$_{2-4}$alkenyl, —CN, —CF$_3$, —NR$^a$R$^b$, —C$_{0-4}$alkylOR$^e$, —C(O)R$^d$ and —C(O)NR$^a$R$^b$;

R$^e$ represents hydrogen or —C$_{1-6}$alkyl;

Y represents a substituent selected from hydrogen, halogen, —C$_{1-4}$alkyl, —C$_{2-4}$alkenyl, —NR$^a$R$^b$, —NO$_2$, —C(O)NR$^a$R$^b$, —N(C$_{1-4}$alkyl)(CHO), —NHCOC$_{1-4}$alkyl, —NHSO$_2$R$^d$, —C$_{0-4}$alkylOR$^e$, —C(O)R$^d$, —S(O)$_n$R$^d$, or —S(O)$_2$NR$^a$R$^b$;

R$^d$ represents —C$_{1-6}$alkyl;

and/or pharmaceutically acceptable derivative thereof.

In one aspect of the invention, R$^1$ represents a group selected from:

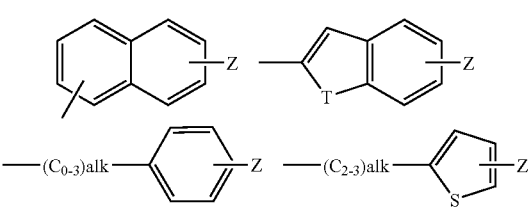

each ring of which optionally contains a further heteroatom N,

Z represents an optional substituent halogen, alk represents alkylene or alkenylene, T represents S, O or NH.

In another aspect of the invention, $R^1$ represents a group selected from:

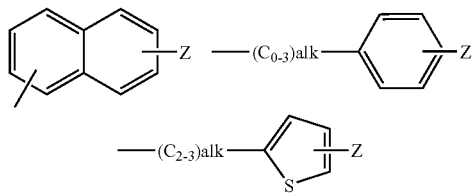

each ring of which optionally contains a further heteroatom N,

Z represents an optional substituent halogen, alk represents alkylene or alkenylene.

In another aspect, $R^1$ represents a group selected from:

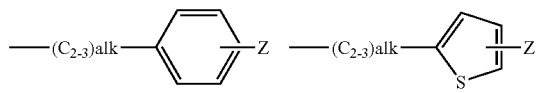

Z represents an optional substituent halogen, alk represents alkylene or alkenylene.

In another aspect, $R^1$ represents:

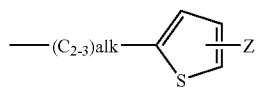

Z represents an optional substituent halogen, alk represents alkylene or alkenylene.

In one aspect of the invention, $R^2$ represents —$C_{1-6}$alkyl, —$C_{0-3}$alkyl$R^c$, $C_{1-3}$alkyl$R^f$, —$C_{2-3}$alkylNR$^a$R$^b$, —$C_{2-3}$alkylOC$_{1-3}$alkyl, —$C_{2-3}$alkylOC$_{1-3}$alkylCONR$^a$R$^b$. In another aspect, $R^2$ represents —$C_{0-3}$alkyl$R^c$, $C_{1-3}$alkyl$R^f$, —$C_{2-3}$alkylNR$^a$R$^b$, —$C_{2-3}$alkylOC$_{1-6}$alkyl, —$C_{2-3}$alkylOC$_{1-3}$alkylCONR$^a$R$^b$. In another aspect, $R^2$ represents —$C_{0-3}$alkyl$R^f$, —$C_{2-3}$alkylOC$_{1-6}$alkyl, —$C_{2-3}$alkylOC$_{1-3}$ alkyl-CONR$^a$R$^b$.

In one aspect of the invention, $R^a$ and $R^b$ independently represent hydrogen or —$C_{1-6}$alkyl.

In one aspect of the invention, $R^a$ represents —$C_{3-5}$cycloalkyl.

In one aspect of the invention, $R^f$ represents a 5- or 6-membered aromatic heterocyclic ring, containing at least one heteroatom selected from O or N, optionally substituted by 0 to 2 substituents selected from —$C_{1-4}$alkyl or —$NH_2$. In another aspect, $R^f$ represents an aromatic heterocyclic ring selected from isoxazole, imidazole, pyrazine or pyridine and is optionally substituted by —$C_{1-4}$alkyl or —$NH_2$.

In one aspect of the invention, X represents phenyl or a 5 or 6 membered aromatic heterocyclic group containing at least one heteroatom selected from O, N or S, each of which is optionally substituted by 0-2 groups selected from: halogen, —$C_{1-4}$alkyl or —NR$^a$R$^b$.

In another aspect, X represents phenyl substituted by a halogen. In another aspect, X represents phenyl substituted by a fluorine.

In one aspect of the invention, Y represents a substituent selected from —C(O)NR$^a$R$^b$, —S(O)$_n$R$^d$, —S(O)$_2$NR$^a$R$^b$, —N(C$_{1-4}$alkyl)(CHO) or —NHSO$_2$R$^d$. In another aspect, Y represents a substituent —C(O)NR$^a$R$^b$.

It Is to be understood that the present Invention covers all combinations of the various aspects of the invention described herein above.

The compounds of formula (I) contain chiral (asymmetric) centres. The individual stereoisomers (enantiomers and diastereoisomers) and mixtures of these are within the scope of the present invention. In one aspect of the invention, the stereochemistry is (S) at the 3-position on the 2-oxopyrrolidine ring (*)

As used herein, the term "alkyl" means both straight and branched chain saturated hydrocarbon groups. Examples of alkyl groups include methyl (—$CH_3$), ethyl (—$C_2H_5$), propyl (—$C_3H_7$) and butyl (—$C_4H_9$).

As used herein, the term "alkylene" means both straight and branched chain saturated hydrocarbon linker groups. Examples of alkylene groups include methylene (—$CH_2$—), ethylene (—$CH_2CH_2$—), and propylene (—$CH_2CH_2CH_2$—).

As used herein, the term "alkenylene" means both straight and branched chain, unsaturated hydrocarbon linker groups, wherein the unsaturation is present only as double bonds. Examples of alkenylene groups Includes ethenylene (—CH═CH—) and propenylene (—$CH_2$—CH═CH—).

As used herein, the term "heterocyclic group" means optionally substituted rings containing one or more heteroatoms selected from: nitrogen, sulphur and oxygen atoms. The heterocycle may be aromatic or non-aromatic, i.e., may be saturated, partially or fully unsaturated. Examples of 5-membered groups include thienyl, furanyl, pyrrolidinyl thiazolyl, oxazolyl and imidazolyl. Examples of 6-membered groups include pyridyl, piperidinyl, pyrimidinyl and morpholinyl. Examples of 7-membered groups include hexamethyleneiminyl. Certain heterocyclic groups, e.g. thienyl, furanyl, thiazolyl, oxazolyl, pyridyl and pyrimidinyl are C-linked to the rest of the molecule. Other heterocyclic groups, e.g pyrrolidinyl, imidazolyl, piperidyl, morpholinyl and hexamethyleneiminyl may be C-linked or N-linked to the rest of the molecule.

As used herein, the term "cycloalkyl group" means an aliphatic ring (a saturated carbocyclic group). Examples of cycloalkyl groups include cyclopropyl, cyclobutyl, cyclopentyl and cyclohexyl.

As used herein, the term "halogen" means an atom selected from fluorine, chlorine, bromine and iodine.

As used herein, the term "pharmaceutically acceptable" means a compound which is suitable for pharmaceutical use.

As used herein, the term "pharmaceutically acceptable derivative", means any pharmaceutically acceptable salt, solvate, or prodrug e.g. ester or carbamate, or salt or solvate of such a prodrug, of a compound of formula (I), which upon administration to the recipient is capable of providing (directly or indirectly) a compound of formula (I), or an active metabolite or residue thereof. Preferred pharmaceutically acceptable derivatives are salts, solvates, esters and carbamates. Particularly preferred pharmaceutically acceptable derivatives are salts, solvates and esters. Most preferred pharmaceutically acceptable derivatives are salts and solvates.

Suitable salts according to the invention Include those formed with both organic and Inorganic acids and bases.

Pharmaceutically acceptable acid addition salts include those formed from mineral acids such as: hydrochloric, hydrobromic, sulphuric, phosphoric, acid; and organic acids such as: citric, tartaric, lactic, pyruvic, acetic, trifluoroacetic, succinic, oxalic, formic, fumaric, maleic, oxaloacetic, methanesulphonic, ethanesulphonic, p-toluenesulphonic, benzenesulphonic and isethionic acids. Particularly preferred pharmaceutically acceptable salts include those formed from hydrochloric, trifluoroacetic and formic acids.

Those skilled in the art of organic chemistry will appreciate that many organic compounds can form, complexes with solvents in which they are reacted or from which they are precipitated or crystallized. These complexes are known as "solvates". For example, a complex with water is known as a "hydrate". Solvates of the compound of formula (I) are within the scope of the invention.

Salts and solvates of compounds of formula (I) which are suitable for use in medicine are those wherein the counterion or associated solvent is pharmaceutically acceptable. However, salts and solvates having non-pharmaceutically acceptable counterions or associated solvents are within the scope of the present invention, for example, for use as intermediates In the preparation of other compounds of formula (I) and their pharmaceutically acceptable salts and solvates.

As used herein, the term "prodrug" means a compound which is converted within the body, e.g. by hydrolysis in the blood, into its active form that has medical effects. Pharmaceutically acceptable prodrugs are described in T. Higuchi and V. Stella, Prodrugs as Novel Delivery Systems, Vol. 14 of the A.C.S. Symposium Series, Edward B. Roche, ed., Bioreversible Carriers in Drug Design, American Pharmaceutical Association and Pergamon Press, 1987, and in D. Fleisher, S. Ramon and H. Barbra "Improved oral drug delivery: solubility limitations overcome by the use of prodrugs", Advanced Drug Delivery Reviews (1996) 19(2) 115-130, each of which are incorporated herein by reference.

Prodrugs are any covalently bonded carriers that release a compound of structure (I) in vivo when such prodrug is administered to a patient. Prodrugs are generally prepared by modifying functional groups in a way such that the modification is cleaved, either by routine manipulation or in vivo, yielding the parent compound. Prodrugs include, for example, compounds of this Invention wherein hydroxyl or amine groups are bonded to any group that, when administered to a patient, cleaves to form the hydroxyl or amine groups.

Esters may be active in their own right and/or be hydrolysable under in vivo conditions In the human body. Suitable pharmaceutically acceptable in vivo hydrolysable ester groups include those which break down readily in the human body to leave the parent acid or its salt. An ester may be formed at a carboxylic acid (—COOH) group or a hydroxyl (—OH) group, by methods well known in the art involving reaction with the corresponding, alcohol, acid, acid chloride, anhydride, or amide. Preferred esters are $C_{1-6}$alkyl esters, e.g. methyl esters, ethyl esters, and the like.

Preferred compounds of the invention include:
4-{(3S)-3-[{[(1E)-2-(5-Chloro-2-thienyl)-1-propen-1-yl]sulfonyl}(cyclopropylmethyl)amino]-2-oxo-1-pyrrolidinyl}-3-fluoro-N,N-dimethylbenzamide;
4-((3S)-3-{{[(1E)-2-(5-Chloro-2-thienyl)-1-propen-1-yl]sulfonyl}[3-(dimethylamino)propyl]amino}-2-oxo-1-pyrrolidinyl)-3-fluoro-N,N-dimethylbenzamide;
4-((3S)-3-{{[(1E)-2-(5-Chloro-2-thienyl)-1-propen-1-yl]sulfonyl}[2-(dimethylamino)ethyl]amino}-2-oxo-1-pyrrolidinyl)-3-fluoro-N,N-dimethylbenzamide;
4-[(3S)-3-({2-[(2-Amino-2-oxoethyl)oxy]ethyl}{[(1E)-2-(5-chloro-2-thienyl)-1-propen-1-yl]sulfonyl}amino)-2-oxo-1-pyrrolidinyl]-3-fluoro-N,N-dimethylbenzamide;
4{(3S)-3-[{[(1E)-2-(5-Chloro-2-thienyl)-1-propen-1-yl]sulfonyl}(cyclopentyl)amino]-2-oxo-1-pyrrolidinyl}-3-fluoro-N,N-dimethylbenzamide;
4-((3S)-3-{{([(1E)-2-(5-Chloro-2-thienyl)-1-propen-1-yl]sulfonyl}[(1-methyl-1H-imidazol-2-yl)methyl]amino}2-oxo-1-pyrrolidiny)-3-fluoro-N,N-dimethylbenzamide;
4{(3S)-3-[{[(1E)-2-(5-Chloro-2-thienyl)-1-propen-1-yl]sulfonyl}(1-methylethyl)amino]-2-oxo-1-pyrrolidinyl}-3-fluoro-N,N-dimethylbenzamide;
4-{(3S)-3-[{[(1E)-2-(5-Chloro-2-thienyl)-1-propen-1-yl]sulfonyl}(2-pyridinylmethyl)amino]-2-oxo-1-pyrrolidinyl}-3-fluoro-N,N-dimethylbenzamide;
4-((3S)-3-{{([(1E)-2-(5-Chloro-2-thienyl)-1-propen-1-yl]sulfonyl}[(3,5-dimethyl-4-isoxazolyl)methyl]amino}-2-oxo-1-pyrrolidinyl)-3-fluoro-N,N-dimethylbenzamide;
4-((3S)-3-{{[(1E)-2-(5-Chloro-2-thienyl)-1-propen-1-yl]sulfonyl}[2-(methyloxy)ethyl]amino}-2-oxo-1-pyrrolidinyl)-3-fluoro-N,N-dimethylbenzamide;
4-[(3S)-3-({[(1E)-2-(5-Chloro-2-thienyl)-1-propen-1-yl]sulfonyl}{2-[(1,1-dimethylethyl)oxy]ethyl}amino)-2-oxo-1-pyrrolidinyl]-3-fluoro-N,N-dimethylbenzamide;
4-[(3S)-3-([(3-Amino-2-pyrazinyl)methyl]{[(1E)-2-(5-chloro-2-thienyl)-1-propen-1-yl]sulfonyl}amino)-2-oxo-1-pyrrolidinyl]-3-fluoro-N,N-dimethylbenzamide;
4-{(3S)-3-[{[(1E)-2-(5-Chloro-2-thienyl)-1-propen-1-yl]sulfonyl}(methyl)amino]-2-oxo-1-pyrrolidinyl}-3-fluoro-N,N-dimethylbenzamide; and
4-{(3S)-3-[{[(E)-2-(5-chloro-2-thienyl)ethenyl]sulfonyl}(methyl)amino]-2-oxo-1-pyrrolidinyl}-3-fluoro-N,N-dimethylbenzamide.

Compounds of the Invention may show advantageous properties, they may be more efficacious, may show greater selectivity, may have fewer side effects, may have a longer duration of action, may be more bioavailable by the preferred route, or may have other more desirable properties than similar known compounds.

The compounds of formula (I) are Factor Xa inhibitors and as such are useful in the treatment of clinical conditions susceptible to amelioration by administration of a Factor Xa inhibitor. Such conditions include acute vascular diseases such as acute coronary syndromes (for example primary and secondary prevention of myocardial infarction and unstable angina and treatment of prothrombotic sequalae associated with myocardial infarction or heart failure), thromboembolism, acute vessel closure associated with thrombolytic therapy and percutaneous transluminal coronary angioplasty (PTCA), transient ischemic attacks, pulmonary embolism, deep vein thrombosis, peripheral arterial occlusion, prevention of vessel luminal narrowing (restenosis), and the prevention of thromboembolic events associated with atrial fibrillation, e.g. stroke; in preventing thrombosis and complications in patients genetically predisposed to arterial thrombosis or venous thrombosis and patients that have a disease-associated predisposition to thrombosis (e.g. type 2 diabetics); the treatment of pulmonary fibrosis; the treatment of tumour metastasis; inflammation; atherosclerosis; neurogenerative disease such as Parkinson's and Alzheimer's diseases; Kasabach Merritt Syndrome; Haemolytic uremic syndrome; endothelial dysfunction; as anticoagulants for extracorporeal blood in for example, dialysis, blood filtration, bypass, and blood product storage; and in the coating of invasive devices such as prostheses, artificial valves and catheters in reducing the risk of thrombus formation.

Accordingly, one aspect of the present invention provides a compound of formula (I) and/or a pharmaceutically acceptable derivative thereof for use in medical therapy, particularly for use in the amelioration of a clinical condition in a mammal, including a human, for which a Factor Xa inhibitor is indicated.

In another aspect, the invention provides a method for the treatment and/or prophylaxis of a mammal, including a human, suffering from a condition susceptible to amelioration by a Factor Xa inhibitor which method comprises administering to the subject an effective amount of a compound of formula (I) or a pharmaceutically acceptable derivative thereof.

In another aspect, the present Invention provides the use of a compound of formula (I) and/or a pharmaceutically acceptable derivative thereof, for the manufacture of a medicament for the treatment and/or prophylaxis of a condition susceptible to amelioration by a Factor Xa inhibitor.

In one aspect of the invention, the condition susceptible to amelioration by a Factor Xa inhibitor is selected from treatment of acute vascular diseases such as acute coronary syndromes (for example primary and secondary prevention of myocardial infarction and unstable angina and treatment of prothrombotic sequalae associated with myocardial infarction or heart failure), thromboembolism, acute vessel closure associated with thrombolytic therapy and percutaneous transluminal coronary angioplasty, transient ischemic attacks, pulmonary embolism, deep vein thrombosis, peripheral arterial occlusion, prevention of vessel luminal narrowing (restenosis), and the prevention of thromboembolic events associated with atrial fibrillation, e.g. stroke.

In another aspect, the condition susceptible to amelioration by a Factor Xa inhibitor is selected from acute coronary syndromes (for example primary and secondary prevention of myocardial infarction and unstable angina and treatment of prothrombotic sequalae associated with myocardial infarction or heart failure), pulmonary embolism, deep vein thrombosis and the prevention of thromboembolic events associated with atrial fibrillation, e.g. stroke.

It will be appreciated that reference to treatment includes acute treatment or prophylaxis as well as the alleviation of established symptoms.

While it is possible that, for use In therapy, a compound of the present invention may be administered as the raw chemical, it is preferable to present the active ingredient as a pharmaceutical formulation.

In a further aspect, the invention provides a pharmaceutical composition comprising at least one compound of formula (I) or a pharmaceutically acceptable derivative thereof in association with a pharmaceutically acceptable carrier and/or excipient. The carrier and/or excipient must be "acceptable" in the sense of being compatible with the other ingredients of the formulation and not deleterious to the recipient thereof.

Accordingly, the present invention further provides a pharmaceutical formulation comprising at least one compound of formula (I) and/or a pharmaceutically acceptable derivative thereof, in association with a pharmaceutically acceptable carrier and/or excipient. The carrier and/or excipient must be "acceptable" in the sense of being compatible with the other Ingredients of the formulation and not deleterious to the recipient thereof.

In another aspect, the invention provides a pharmaceutical composition comprising, as active ingredient, at least one compound of formula (I) and/or a pharmaceutically acceptable derivative thereof in association with a pharmaceutically acceptable carrier and/or excipient for use in therapy, and in particular in the treatment of human or animal subjects suffering from a condition susceptible to amelioration by a Factor Xa inhibitor.

There is further provided by the present invention a process of preparing a pharmaceutical composition, which process comprises mixing at least one compound of formula (I) and/or a pharmaceutically acceptable derivative thereof, together with a pharmaceutically acceptable carrier and/or excipient.

The compounds for use according to the present invention may be formulated for oral, buccal, parenteral, topical, rectal or transdermal administration or in a form suitable for administration by inhalation or insufflation (either through the mouth or the nose).

For oral administration, the pharmaceutical compositions may take the form of, for example, tablets or capsules prepared by conventional means with pharmaceutically acceptable excipients such as binding agents (e.g. pregelatinised maize starch, polyvinylpyrrolidone or hydroxypropyl methylcellulose); fillers (e.g. lactose, microcrystalline cellulose or calcium hydrogen phosphate); lubricants (e.g. magnesium stearate, talc or silica); disintegrants (e.g. potato starch or sodium starch glycollate); or wetting agents (e.g. sodium lauryl sulphate). The tablets may be coated by methods well known in the art. Liquid preparations for oral administration may take the form of, for example, solutions, syrups or suspensions or they may be presented as a dry product for constitution with water or other suitable vehicles before use. Such liquid preparations may be prepared by conventional means with pharmaceutically acceptable additives such as suspending agents (e.g. sorbitol syrup, cellulose derivatives or hydrogenated edible fats); emulsifying agents (e.g. lecithin or acacia); non-aqueous vehicles (e.g. almond oil, oily esters, ethyl alcohol or fractionated vegetable oils); and preservatives (e.g. methyl or propyl-p-hydroxybenzoates or sorbic acid). The preparations may also contain buffer salts, flavouring, colouring and sweetening agents as appropriate.

Preparations for oral administration may be suitably formulated to give controlled/extended release of the active compound.

For buccal administration the compositions may take the form of tablets or lozenges formulated in a conventional manner.

The compounds according to the present Invention may be formulated for parenteral administration by injection, e.g. by bolus injection or continuous infusion. Formulations for injection may be presented in unit dosage form, e.g. in ampoules or in multi-dose containers, with an added preservative. The compositions may take such forms as suspensions, solutions or emulsions in oily or aqueous vehicles, and may contain formulatory agents such as suspending, stabilising and/or dispersing agents. Alternatively, the active ingredient may be in powder form for constitution with a, suitable vehicle, e.g. sterile pyrogen-free water, before use.

The compounds according, to the present Invention may be formulated for topical administration by insufflation and inhalation. Examples of types of preparation for topical administration include sprays and aerosols for use in an inhaler or insufflator.

Powders for external application may be formed with the aid of any suitable powder base, for example, lactose, talc or starch. Spray compositions may be formulated as aqueous solutions or suspensions or as aerosols delivered from pressurised packs, such as metered dose inhalers, with the use of a suitable propellant.

The compounds according to the present invention may also be formulated In rectal compositions such as suppositories or retention enemas, e.g. containing conventional suppository bases such as cocoa butter or other glycerides.

In addition to the formulations described previously, the compounds may also be formulated as a depot preparation. Such long acting formulations may be administered by implantation (for example subcutaneously, transcutaneously or intramuscularly) or by intramuscular injection. Thus, for example, the compounds according to the present invention may be formulated with suitable polymeric or hydrophobic materials (for example as an emulsion in an acceptable oil) or ion exchange resins or as sparingly soluble derivatives, for example, as a sparingly soluble salt.

A proposed dose of the compounds according to the present invention for administration to a human (of approximately 70 kg body weight) is 0.1 mg to 1 g, such as 1 mg to 500 mg of the active ingredient per unit dose, expressed as the weight of free base. The unit dose may be administered, for example, 1 to 4 times per day. The dose will depend on the route of administration. It will be appreciated that it may be necessary to make routine variations to the dosage depending on the age and weight of the patient as well as the severity of the condition to be treated. The dosage will also depend on the route of administration. The precise dose and route of administration will ultimately be at the discretion of the attendant physician or veterinarian.

The compounds of formula (I) may also be used in combination with other therapeutic agents. The invention thus provides, in a further aspect, a combination comprising a compound of formula (I) and/or a pharmaceutically acceptable derivative thereof together with one or more further therapeutic agent(s).

When a compound of formula (I) and/or a pharmaceutically acceptable derivative thereof is used in combination with a second therapeutic agent the dose of each compound may differ from that when the compound is used alone. Appropriate doses will be readily appreciated by those skilled in the art. It will be appreciated that the amount of a compound of the invention required for use in treatment will vary with the nature of the condition being treated and the age and the condition of the patient and will be ultimately at the discretion of the attendant physician or veterinarian. The compounds of the present invention may be used in combination with other antithrombotic drugs (such as thrombin inhibitors, thromboxane receptor antagonists, prostacyclin mimetics, phosphodiesterase inhibitors, fibrinogen antagonists, thrombolytic drugs such as tissue plasminogen activator and streptokinase, non-steroidal anti-inflammatory drugs such as aspirin, and the like), anti-hypertensive agents (such as angiotensin-converting enzyme inhibitors, angiotensin-II receptor antagonists, ACE/NEP inhibitors, β-blockers, calcium channel blockers, PDE inhibitors, aldosterone blockers), anti-atherosclerotic/dyslipidaemic agents (such as HMG-CoA reductase inhibitors) and anti-arrhythmic agents.

The combinations referred to above may conveniently be presented for use in the form of a pharmaceutical formulation and thus pharmaceutical formulations comprising a combination as defined above together with at least one pharmaceutically acceptable carrier and/or excipient comprise a further aspect of the invention. The Individual components of such combinations may be administered either sequentially or simultaneously in separate or combined pharmaceutical formulations by any convenient route.

When administration is sequential, either the Factor Xa inhibitor or the second therapeutic agent may be administered first. When administration is simultaneous, the combination may be administered either in the same or different pharmaceutical composition.

When combined in the same formulation it will be appreciated that the two compounds must be stable and compatible with each other and the other components of the formulation. When formulated separately they may be provided in any convenient formulation, conveniently in such manner as are known for such compounds in the art.

The compounds of formula (I) and/or pharmaceutically acceptable derivatives thereof may be prepared by the processes described hereinafter, said processes constituting a further aspect of the invention. In the following description, the groups are as defined above for compounds of formula (I) unless otherwise stated.

According to a further aspect of the present invention, there is provided a process (A) for preparing compounds of formula (I) which comprises reacting a compound of formula (II) with a compound of formula (III):

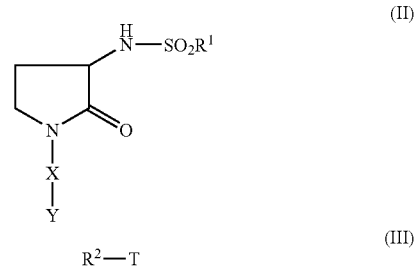

where $R^2$ is other than hydrogen and T is a suitable leaving group such as that derived from a hydroxyl group or a halide, e.g. bromide. When T is halide, the reaction is effected in a suitable organic solvent, e.g. THF or DMF, In the presence of a base, e.g. lithium hexamethyldisilylamide (LiHMDS), potassium carbonate or sodium carbonate, at a temperature range from −78° C. to +50° C. When T is a hydroxyl group, the reaction Is effected under Mitsunobu conditions (for examples see Hughes, David L. Progress in the Mitsunobu reaction. A review. Organic Preparations and Procedures International (1996), 28(2), 127-64.). For example, the reaction may be performed by treatment of compounds of formula (I) where $R^2$ represents H with an aryl or alkyl phosphine, e.g. triphenylphosphine, optionally bound to polymer-support, and an azodicarboxylate derivative, e.g. bis (1,1-dimethylethyl) (E)-1,2-diazene dicarboxylate or N,N-di-tert-butyl azodicarboxylate, in a suitable solvent, e.g. dichloromethane (DCM) or tetrahydrofuran (THF), followed by addition of a compound of formula (III) where T represents OH, optionally in a suitable solvent, e.g. THF, suitably at room temperature.

When X-Y contains a group reactive to compounds of formula (III), such groups may be protected prior to the reaction using methods well known in the art and such protecting groups removed under standard conditions to provide compounds of formula (I) where $R^2$ is a substituent other than hydrogen after completion of the reaction of a compound of formula (III) where $R^2$ is hydrogen with a compound of formula (II).

A compound of formula (II) may be prepared by reacting a compound of formula (IV) or an acid addition salt thereof with a compound of formula (V) where V is a suitable leaving group, such as a halide, e.g. chloride. When the free base of a compound of formula (IV) is used, the reaction is conveniently carried out in the presence of a base, e.g. pyridine, and in a suitable solvent, e.g. acetonitrile (MeCN), suitably at 0° C. to room temperature. When the acid addition salt of a compound of formula (IV) is used, the reaction is conveniently carried out in the presence of a base, e.g. N,N-diisopropylethylamine (DIPEA), optionally in the presence of pyridine, and in a suitable solvent, e.g. MeCN, suitably at 0° C. to room temperature.

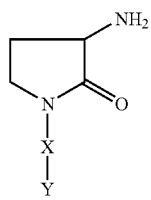

(IV)

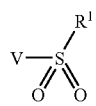

(V)

If X-Y contains a group reactive to compounds of formula (V), such groups may be protected prior to reaction of a compound of formula (IV) with a compound of formula (V) using methods well known in the art and such protecting groups removed under standard conditions to provide compounds of formula (II) after completion of the reaction of a compound of formula (IV) with a compound of formula (V).

Compounds of formula (V) are known compounds or may be prepared by methods known in the literature or processes known to those skilled in the art.

Compounds of formula (IV) may be prepared from compounds of formula (VI):

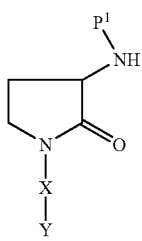

(VI)

wherein $P^1$ is a suitable amine protecting group, e.g. Boc (t-butyloxycarbonyl), by removal of the protecting group under standard conditions. For example, when $P^1$ represents Boc, removal of the protecting group may be effected under acidic conditions, using for example hydrochloric acid in a solvent such as dioxan, suitably at 0° C. to room temperature.

Compounds of formula (VI) where Y represents —CON-$R^aR^b$ may be prepared from compounds of formula (VII):

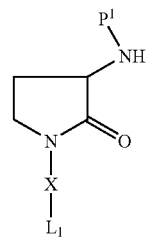

(VII)

where $L_1$ is a suitable leaving group, such as halide, e.g. iodide, by reaction with $HNR^aR^b$, suitably in excess, in a suitable, solvent, e.g. N,N-dimethylformamide (DMF) in the presence of a transition metal catalyst or its salt ligand complex, e.g. bis(triphenylphosphine)palladium(II) chloride, and in an atmosphere of carbon monoxide, suitably at elevated temperature e.g. 60-100° C.

Compounds of formula $HNR^aR^b$ are known compounds or may be prepared by methods known in the literature or processes known to those skilled in the art.

Compounds of formula (VII) may be prepared from compounds of formula (VIII):

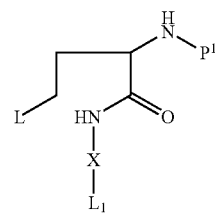

(VIII)

by cyclisation where L represents a suitable leaving group. For example when L Is a hydroxyl group, the ring closure may be performed by treatment with a mixture of (i) aryl or alkyl phosphine, e.g. tri-n-butylphosphine, and (ii) a suitable azodicarboxylate derivative, e.g. 1,1'-(azodicarbonyl)-dipiperidine, in a suitable solvent, e.g. THF, suitably at 0° C. to room temperature.

It will be appreciated by persons skilled in the art that compounds of formula (VIII) may be prepared by interconversion, utilising other compounds of formula (VII) which are optionally protected by standard protecting groups, as precursors. For instance, compounds of formula (VII) where L is OH, may be converted into compounds of formula (VIII) possessing alternative substituents at L, e.g. halogen, $S^+MeR$ $W^-$ or $OSO_2R$, by methods well known in the art (see for example Smith, M. B. and March, J., Advanced Organic Chemistry, 5th Edition 2001, John Wiley & Sons). Generally R will represent alkyl or aralkyl and W will represent sulphate or halide, especially iodide. In such cases the ring closure may be performed by treatment with a base in a suitable solvent, e.g. MeCN.

Compounds of formula (VIII), where L is a hydroxyl group, may be prepared by reacting a compound of formula (IX) with a compound of formula (X):

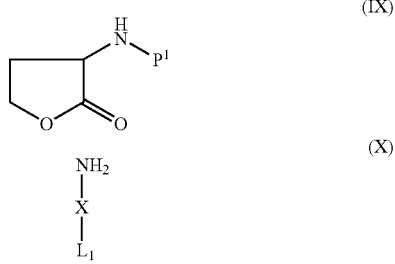

wherein $P^1$ is a suitable protecting group as described above. The reaction is conveniently carried out by addition of a suitable activating agent, e.g. trimethylaluminium, to compounds of formula (X) in a suitable solvent, e.g. DCM, under an inert atmosphere, e.g. nitrogen, suitably at room temperature followed by addition of a compound of formula (IX) in a compatible solvent, e.g. DCM.

Compounds of formula (X) are known compounds or may be prepared by methods known In the literature or processes known to those skilled in the art.

Compounds of formula (IX) may be prepared from compounds of formula (XI) where HA is a suitable acid, e.g. hydrochloric acid, using methods well known to those skilled in the art. See, for example, "Protective groups in organic synthesis" by T. W. Greene and P. G. M. Wuts (John Wiley & sons 1991) or "Protecting Groups" by P. J. Kocienski (Georg Thieme Verlag 1994).

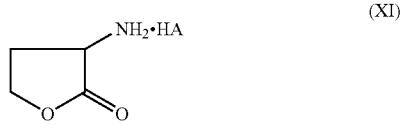

Compounds of formula (XI) are known compounds or may be prepared by methods known in the literature or processes known to those skilled in the art.

There is provided a further process (B), for preparing compounds of formula (VI) where Y represents $CONR^aR^b$, by reaction of compounds of formula (XII) with $HNR^aR^b$ or an acid addition salt thereof:

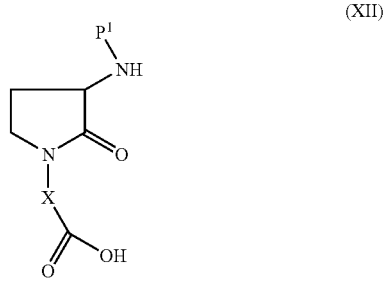

In a suitable solvent, e.g. N,N-dimethylformamide (DMF), in the presence of a base, e.g. N,N-diisopropylethylamine (DIPEA), and in the presence of a carboxylic acid activating agent, e.g. N-[1H-1,2,3-benzotriazol-1-yloxy (dimethylamino)methylidene]-N-methylmethanaminium tetrafluoroborate (TBTU), suitably at room temperature and using protecting groups where appropriate. It will be understood by persons skilled in the art, that if $R^a$ and $R^b$ contain a group(s) reactive to reagents used during the above reaction conditions, such groups may be protected prior to using methods well known in the art and removed under standard conditions after completion of the reaction.

Alternatively, compounds of formula (VI) where Y represents $CONR^aR^b$, may be prepared by reaction of compounds of formula (XII) with $HNR^aR^b$ or an acid addition salt thereof in a suitable solvent, e.g. MeCN, in the presence of a base, e.g. 1-(3-dimethylaminopropyl)-3-ethyl carbodiimide, and in the presence of a carboxylic acid activating agent, e.g. 1-hydroxybenzotriazole, suitably at room temperature and using protecting groups where appropriate. It will be understood by persons skilled in the art, that if $R^a$ and $R^b$ contain a group(s) reactive to reagents used during the above reaction conditions, such groups may be protected prior to using methods well known in the art and removed under standard conditions after completion of the reaction.

Compounds of formula (XII) may be prepared from compounds of formula (XII):

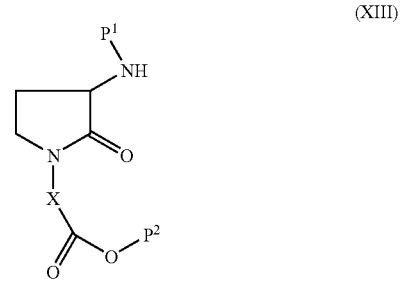

where $P^2$ is a suitable carboxylic acid protecting group e.g. benzyl, by removal of the protecting group under standard conditions. For example, when $P^2$ represents benzyl, removal of the protecting group may be effected by hydrogenolysis using a suitable catalyst, e.g. 20% palladium hydroxide on carbon, in a suitable solvent such as ethanol, suitably at atomospheric pressure and room temperature.

Compounds of formula (XIII) may be prepared from compounds of formula (XIV):

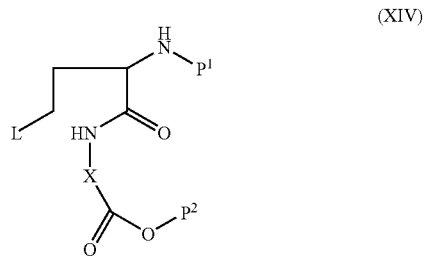

where L represents a suitable leaving group, by cyclisation. For example, when L is a hydroxyl group, the ring closure may be performed by treatment with a mixture of (i) aryl or alkyl phosphine, e.g. tri-n-butylphosphine, and (ii) a suitable azodicarboxylate derivative, e.g. 1,1'-(azodicarbonyl)-dipiperidine, in a suitable solvent, e.g. tetrahydrofuran (THF), suitably at 0° C. to room temperature.

It will be appreciated by persons skilled in the art that compounds of formula (XV) may be prepared by interconversion, utilising other compounds of formula (XV) which are optionally protected by standard protecting groups, as precursors. For instance, compounds of formula (XV) where L is OH, may be converted into compounds of formula (XV) possessing alternative substituents at L, e.g. halogen, $S^+MeR\ W^-$ or $OSO_2R$, by methods well known in the art (see for example Smith, M. B. and March, J., Advanced Organic Chemistry, 5$^{th}$ Edition 2001, John Wiley & Sons). Generally R will represent alkyl or aralkyl and W will represent sulphate or halide, especially iodide. In such cases the ring closure may be performed by treatment with a base in a suitable solvent, e.g. MeCN.

Compounds of formula (XIV), where L Is a hydroxyl group, may be prepared by reacting a compound of formula (IX) with a compound of formula (XV):

(XV)

where $P^1$ and $P^2$ are a suitable protecting groups as described above. The reaction is conveniently carried out by addition of a suitable activating agent, e.g. trimethylaluminium, to compounds of formula (XV) in a suitable solvent, e.g. DCM, under an inert atmosphere, e.g. nitrogen, suitably at room temperature followed by addition of a compounds of formula (IX) in a compatible solvent, e.g. DCM.

Alternatively, compounds of formula (VI) may be prepared from compounds of formula (XVI):

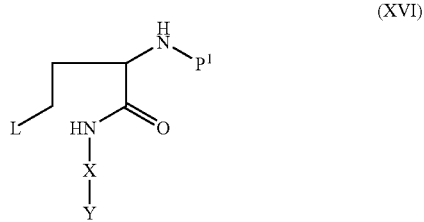

(XVI)

by cyclisation where L represents a leaving group. For example when L is a hydroxyl group, the ring closure may be performed by treatment with an aryl or alkyl phosphine, e.g., tri-n-butylphosphine, and a dialkyl azodicarboxylate, e.g. diisopropyl azodicarboxylate, in a suitable solvent, e.g. THF (tetrahydrofuran).

It will be appreciated by persons skilled in the art that compounds of formula (XVI) may be prepared by interconversion, utilising other compounds of formula (XVI) which are optionally protected by standard protecting groups, as precursors. For instance, compounds of formula (XVI) where L is OH, may be converted into compounds of formula (XVI) possessing alternative substituents at L, e.g. halogen, $^+SMeRW^-$ or $OSO_2R$, by methods well known in the art (see for example Smith, M. B. and March, J., Advanced Organic Chemistry, 5$^{th}$ Edition 2001, John Wiley & Sons). Generally R will represent alkyl or aralkyl and W will represent halide, especially iodide or sulphate. In such cases the ring closure may be performed by treatment with a base in a suitable solvent, e.g. MeCN.

Compounds of formula (XVI) where L is a hydroxyl group, may be prepared by reacting a compound of formula (IX) with a compound of formula (XVII):

(XVII)

wherein $P^1$ is a suitable protecting group as described above. The reaction is conveniently carried out by addition of a Lewis acid, e.g. trimethylaluminium, to compounds of formula (XVII) In a suitable solvent e.g. DCM, under an inert atmosphere, e.g., nitrogen, suitably at room temperature followed by addition of a compounds of formula (IX) in a compatible solvent e.g., DCM.

Compounds of formula (XVII) are known compounds or may be prepared by methods known in the literature or processes known to those skilled in the art.

It will be appreciated that the Y group in compounds of formula (I), (II), (IV), (VI) and (XVI) may be interconverted using methods well known to those skilled in the art (see for example Smith, M. B. and March, J., Advanced Organic Chemistry, 5$^{th}$ Edition 2001, John Wiley & Sons). For example, when Y is $NO_2$, it may be converted to Y is $NH_2$ by reduction with a reductant such as tin (II) chloride suitably in ethyl acetate (EtOAc). When Y is —$NHCOC_{1-4}alkyl$ or —$NHSO_2R^d$, these compounds may be prepared by acylation or sulfonylation where Y is $NH_2$ with $TCOC_{1-4}alkyl$ or $TSO_2R^d$ respectively, where T is a suitable leaving group as defined before. When compounds of formula (I), (II), (IV), (VI) and (XVI) contain a group reactive to reagents used during the interconversion process of Y, such a group may be protected under standard conditions using methods well known to those skilled in the art. See, for example, "Protective groups in organic synthesis" by T. W. Greene and P. G. M. Wuts (John Wiley & sons 1991) or "Protecting Groups" by P. J. Kocienski (Georg Thieme Verlag 1994).

It will be appreciated by those skilled in the art that compounds of formula (I) or a solvate thereof may be synthesized from appropriate intermediates via solid phase chemistry processes.

Those skilled in the art will appreciate that in the preparation of the compound of formula (I) or a solvate thereof it may be necessary and/or desirable to protect one or more sensitive groups in the molecule or the appropriate intermediate to prevent undesirable side reactions. Suitable protecting groups for use according to the present invention are well known to those skilled in the art and may be used in a conventional manner. See, for example, "Protective groups in organic synthesis" by T. W. Greene and P. G. M. Wuts (John Wiley & sons 1991) or "Protecting Groups" by P. J. Kocienski (Georg Thieme Verlag 1994). Examples of suitable amino protecting groups Include acyl type protecting groups (e.g. formyl, trifluoroacetyl, acetyl), aromatic urethane type protecting groups (e.g. benzyloxycarbonyl (Cbz) and substituted Cbz), aliphatic urethane protecting groups (e.g. 9-fluorenylmethoxycarbonyl (Fmoc), t-butyloxycarbonyl (Boc), isopropyloxycarbonyl, cyclohexyloxycarbonyl)

and alkyl or aralkyl type protecting groups (e.g. benzyl, trityl, chlorotrityl). Examples of suitable hydoxyl protecting groups may Include for example alkyl silyl groups, such as trimethylsilyl or tert-butyldimethylsilyl; alkyl ethers such as tetrahydropyranyl or tert-butyl; or esters such as acetate.

Various intermediate compounds used in the above-mentioned process, including but not limited to certain compounds of formulae (II), (IV), (VI), (XII), (XIV), (XV) and (XVI) constitute a further aspect of the present invention.

The present invention will now be further illustrated by the accompanying examples which should not be construed as limiting the scope of the invention in any way.

All publications, including but not limited to patents and patent applications, cited in this specification are herein incorporated by reference as if each individual publication were specifically and individually indicated to be incorporated by reference herein as though fully set forth.

EXAMPLES

| Abbreviations | |
|---|---|
| THF | Tetrahydrofuran |
| DCM | Dichloromethane |
| DMF | N,N-Dimethylformamide |
| MeCN | Acetonitrile |
| DIPEA | N,N-Diisopropylethylamine |
| PS | Polymer supported |
| CBZ | carbobenzyloxy |
| br | broad |
| m | multiplet |
| q | quartet |
| s | singlet |
| t | triplet |
| d | doublet |

Intermediate 1

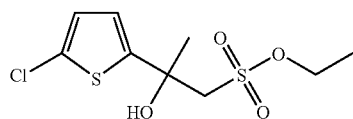

Ethyl 2-(5-chloro-2-thienyl)-2-hydroxy-1-prorane-sulfonate

A solution of ethyl methanesulphonate (4.97 g) in THF (20 ml) was added dropwise to a solution of lithium hexamethyldisilylamide (42.0 ml of 1M solution in THF plus 20 ml of THF) at −78° C. under nitrogen, and the solution was stirred for 30 min. A solution of 2-acetyl-5-chlorothiophene (6.75 g) in THF (70 ml) was added to this over 15 min and the temperature maintained at −78° C. for 90 min. The reaction was quenched with saturated aqueous ammonium chloride and the mixture extracted with ethyl acetate. The combined organic fractions were washed with brine; dried (over magnesium sulphate) and concentrated under reduced pressure to afford a crude oil that was purified by Biotage™ chromatography (silica, eluting with ether-cyclohexane 1:3) to give the title compound (10.9 g) as a colourless oil.

$^1$H NMR (CDCl$_3$): δ6.79 (1H, d), 6.73 (1H, d), 4.26 (2H, m), 4.14 (1H, s), 3.32 (1H, d), 3.52 (1H, d), 1.8 (3H, s), 1.36 (3H, t).

Intermediate 2

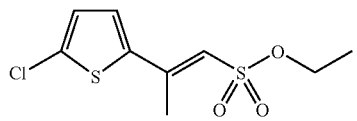

Ethyl (1E)-2-(5-chloro-2-thienyl)-1-propene-1-sulfonate

A solution of Intermediate 1 (10.9 g) in DCM (300 ml) was cooled to 0° C. under nitrogen, to which was added methanesulphonic acid (15.0 ml) in a dropwise fashion. After stirring for 90 min, saturated aqueous sodium bicarbonate was added, followed by water and brine. The layers were separated and the aqueous layer back extracted with DCM; the organic fractions were combined, washed with brine and dried (over magnesium sulphate) and concentrated under reduced pressure. The crude mixture was purified using Biotage™ chromatography (silica, eluting chloroform and 15% tert-butylmethyl ether in cyclohexane) to give the title compound (2.9 g) as a white crystalline solid.

$^1$H NMR (CDCl$_3$): δ7.16 (1H, d), 6.92 (1H, d), 6.47 (1H, d) 4.26 (2H, q), 2.50 (3H, d), 1.42 (3H, t).

Intermediate 3

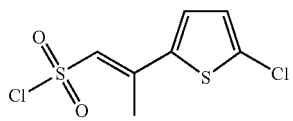

(1E)-2-(5-Chloro-2-thienyl)-1-propene-1-sulfonyl chloride

Tetrabutylammonium iodide (4.03 g) was added to a solution of Intermediate 2 (2.9 g) in acetone (180 ml) under nitrogen and the solution heated under reflux for 17 h. The solution was cooled and concentrated under reduced pressure to produce a yellow-brown solid. This was stirred in phosphorus oxychloride (30 ml) at room temperature for 3.5 h, after which the volatiles were removed under reduced pressure and the residue co-evaporated twice with toluene. The residue was purified using Biotage™ chromatography (silica, eluting with, cyclohexane and cyclohexane:diethyl ether 1:1) to give the title compound (2.1 g) as a yellow crystalline solid.

$^1$H NMR (CDCl$_3$): δ7.31 (1H, d), 6.99 (1H, d), 6.96 (1H, q), 2.64 (3H, d).

Intermediate 4

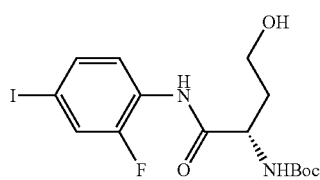

1,1-Dimethylethyl ((1S)-1-{[(2-fluoro-4-iodophenyl)amino]carbonyl}-3-hydroxypropyl)carbamate A solution of 2-fluoro-4-iodoaniline (7.11 g) in anhydrous DCM (40 ml) under N₂ at 0° C. was treated dropwise with trimethylaluminium (2N in heptane; 15 ml). The mixture was allowed to stir for 30 min before a solution of tert-butyl (3S)-2-oxotetrahydrofuran-3-ylcarbamate (5.03 g), in anhydrous DCM (35 ml), was added dropwise. The reaction was allowed to warm up to ambient temperature and stirred for 18 h, before quenching with 10% aqueous citric acid acid (10 ml) Saturated aqueous potassium sodium tartrate (100 ml) was then added with stirring followed by separation of the organic and aqueous layers. The organic layer was dried (over magnesium sulphate) and concentrated under reduced pressure. The residue was purified using Biotage™ chromatography (silica, eluting with cyclohexane:ethyl acetate 3:2) to afford an off-white solid which was an inseparable mixture (c. 1:2) of the starting material and the title compound (5.55 g).

Mass spectrum: Found: MH⁺ 439

Intermediate 5

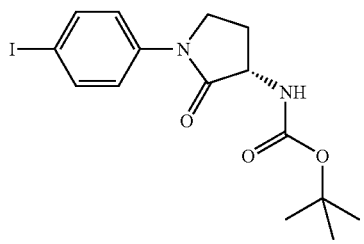

1,1-Dimethylethyl[(3S)-1-(2-fluoro-4-iodophenyl)-2-oxo-3-pyrrolidinyl]carbamate To a solution of crude Intermediate 4 (5.55 g) and tri-n-butylphosphine (3.49 ml) in anhydrous THF (100 ml) under N₂ at 0° C. was added solid 1,1'-(azodicarbonyl)-dipiperidine (3.53 g). The solution was allowed to warm to ambient temperature and stirred for 18 h. The mixture was then diluted with cyclohexane (100 ml) and the precipitate filtered off. The filtrate was then concentrated under reduced pressure and the residue purified using Biotage™ chromatography (silica, eluting with cyclohexane:ethyl acetate 2:1) to give the title compound (2.93 g) as a white solid.

Mass spectrum: Found: MH⁺ 421

Intermediate 6

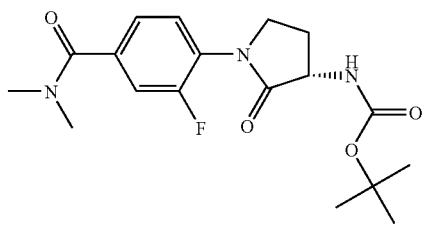

1,1-Dimethylethyl((3S)-1-{4-[(dimethylamino)carbonyl]-2-fluorophenyl}-2-oxo-3-Pyrrolidinyl)carbamate A solution of Intermediate 5 (0.6 g) in dry DMF (8 ml) was treated with dimethylamine (2N in tetrahydrofuran) (3.56 ml) and bis(triphenylphosphine)palladium(II) chloride (0.06 g). Carbon monoxide gas was bubbled through the mixture for 10 min and the reaction was then heated to 80° C., for 18 h, under positive carbon monoxide pressure. The cooled reaction was concentrated under reduced pressure, partitioning the residue between ethyl acetate and water. The separated organic layer was dried (over magnesium sulphate) and concentrated under reduced pressure to give crude material which was dissolved in minimum DCM and loaded onto preconditioned silica phase SPE (eluting with cyclohexane: ethylacetate 10:1, 5:2 and neat ethylacetate) to give the title compound (0.188 g) as a white powder.

Mass spectrum: Found: MH⁺ 366

Alternative Process to Intermediate 6:

To a solution of Intermediate 13 (0.905 g) in acetonitrile (20 ml) was added 1-(3-dimethylaminopropyl)-3-ethyl carbodiimide (0.57 g) and 1-hydroxybenzotriazole (0.4 g). The mixture was stirred for 30 min, treated with a solution solution of dimethylamine (1.5 ml, 2N) in tetrahydrofuran and then stirred for 17 h. The reaction mixture was partitioned between ethyl acetate and hydrochloric acid (2N), the organic phase separated and washed with sodium hydrogen carbonate (satd. sol.) and brine. The combined organic extracts were dried over anhydrous magnesium sulphate, filtered and evaporated under reduced pressure to give the title compound (0.71 g) as a white solid.

Mass spectrum: Found: MH+ 366 H.p.l.c. Rt 2.44 min

Intermediate 7

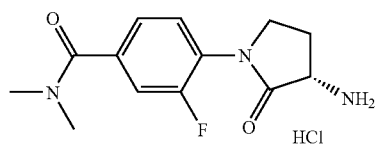

4-[(3S)-3-Amino-2-oxo-1-pyrrolidinyl]-3-fluoro-N,N-dimethylbenzamide hydrochloride A solution of Intermediate 6 (0.188 g) in 4N hydrochloric acid in dioxane (8 ml) was stirred for 2 h at 0° C. before allowing to warm up to room temperature for 2 h. The reaction was concentrated under reduced pressure to give the title compound (0.183 g) as a yellow powder.

Mass spectrum: Found: MH⁺ 266

Intermediate 8

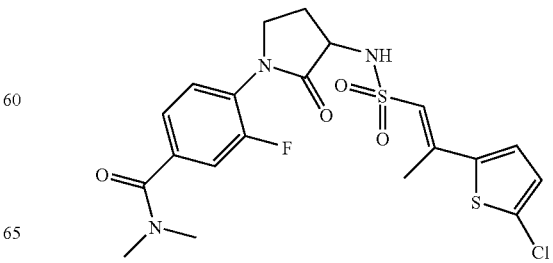

4-[(3S)-3-({[(1E)-2-(5-Chloro-2-thienyl)-1-propen-1-yl]sulfonyl}amino)-2-oxo-1-pyrrolidinyl]-3-fluoro-N,N-dimethylbenzamide A suspension of Intermediate 7 (0.043 g) in dry MeCN (6 ml) at 0° C. was treated with DIPEA (0.025 ml) and pyridine (0.014 ml), stirring for 5 min. Intermediate 3 (0.143 g) was added, in 2 portions, stirring the reaction for 1 h, before warming to room temperature for 18 h. The reaction was concentrated under reduced pressure the residue between DCM and saturated aqueous sodium bicarbonate. The separated organic layer was dried (magnesium sulphate) and concentrated under reduced pressure to give a residue which was purified via mass-directed autoprep to give the title compound (0.038 g) as a white powder.

Mass spectrum: Found: MH⁻ 484 H.p.l.c. (1) Rt 2.98 min

Intermediate 9

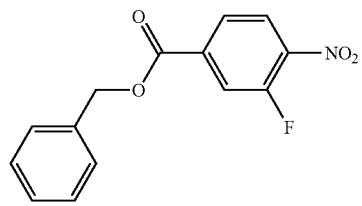

Phenylmethyl 3-fluoro-4-nitrobenzoate

A suspension of 3-fluoro-4-nitroberizoic acid (33.0 g) in anhydrous DMF (300 ml) was cooled to 0° C., treated with sodium bicarbonate (13.5 g) and stirred for 30 min. The mixture was treated dropwise with benzyl bromide (19.0 ml) stirred for a further 30 min then allowed to warm to room temperature while stirring overnight (18 h). The resulting orange solution was evaporated under reduced pressure and the residue partitioned between ethyl acetate (1200 ml) and saturated aqueous sodium carbonate (1600 ml). The organic layer was split into 2×600 ml portions and each was washed with water (2×500 ml), brine (200 ml), dried over anhydrous magnesium sulfate then filtered. The filtrates were combined and evaporated under reduced pressure to give the title compound (38.2 g) as an orange oil which crystallised on standing overnight.

¹H NMR in CDCl₃; δ 8.11 (dd, 1H), 7.99 (m, 2H), 7.48-7.37 (5H), 5.41 (s, 2H) H.p.l.c. Rt 3.45 min Intermediate 10

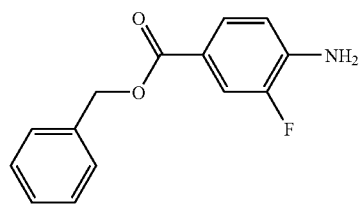

Phenylmethyl 4-amino-3-fluorobenzoate

A solution of Intermediate 9 (38.2 g) in ethyl acetate (1500 ml) was treated portionwise with tin chloride dihydrate (156.5 g) over 10 min. The mixture was heated to reflux for 2.5 h then cooled to room temperature, diluted with ethyl acetate (1000 ml) and treated cautiously with water (1500 ml) and saturated aqueous sodium bicarbonate (1500 ml). The resulting thick suspension was stirred for 10 min then filtered through a pad of celite filteraid. Reaction vessel and filter pad were then washed with ethyl acetate (500 ml) and water (200 ml). The combined filtrates were partitioned, the aqueous layer extracted with ethyl acetate (2×1000 ml) and the combined organic layers dried over anhydrous sodium sulphate, filtered and evaporated to give the title compound (33.7 g) as an orange oil which crystallised on standing overnight.

Mass spectrum: Found: MH⁺ 246 H.p.l.c. Rt 3.25 min

Intermediate 11

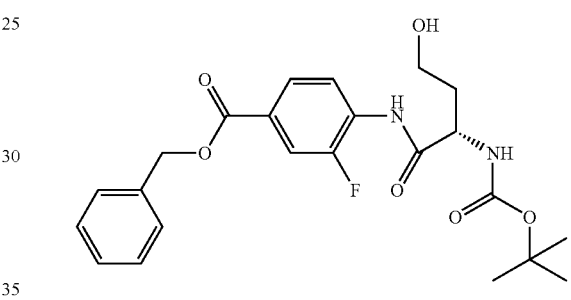

Phenylmethyl 4-[(N-{[(1,1-dimethylethyl)oxy]carbonyl}-L-homoseryl)amino]-3-fluorobenzoate A solution of Intermediate 10 (5.53 g) in anhydrous DCM (40 ml) at room temperature under nitrogen was treated dropwise over 35 min with trimethyl aluminium (2 molar in heptane, 13.5 ml). Slow addition rate and a water bath were used to prevent reaction temperature rising above 30° C. during addition. The mixture was stirred for 30 min then treated with a solution of 1,1-dimethylethyl [(3S)-2-oxotetrahydro-3-furanyl]carbamate (3.87 g) in anhydrous DCM (40 ml), and the final mixture stirred for 20 h before quenching by cautious addition of 5% citric acid solution (100 ml). A fine precipitate formed, this was filtered through a pad of celite filteraid, washed with water (50 ml) and DCM (100 ml). The combined filtrates were partitioned, the aqueous layer extracted with DCM (50 ml), and the combined organic layers were washed With saturated sodium potassium tartrate solution (Rochelle's Salt)(50 ml), brine (50 ml) then dried over anhydrous magnesium sulfate, filtered and evaporated under reduced pressure to give a crude yellow oil (7.45 g). Purification by Quad Biotage™ chromatography (2×90 g Si) eluting with 1% methanol in DCM gave the title compound (2.11 g) as a pale yellow foam.

Mass spectrum: Found: MH⁺ 447 H.p.l.c. Rt 3.27 min

Intermediate 12

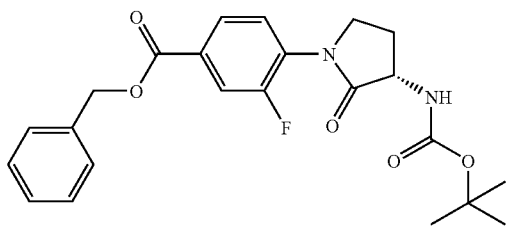

Phenylmethyl 4-[(3S)-3-({[(1,1-dimethylethyl)oxy]carbonyl}amino)-2-oxo-1-pyrrolidinyl]-3-fluorobenzoate A solution of 1,1'(azodicarbonyl)dipiperidine (1.42 g) in anhydrous THF (15 ml) under nitrogen was cooled to 0° C. and treated with tri-n-butylphosphine (1.40 ml), giving a deep yellow solution which was stirred for 20 min. The now clear solution was treated with a solution of Intermediate 11 (2.10 g) in anhydrous THF (15 ml), giving a viscous mixture. Stirring was continued for 30 min below 5° C. and then for 20 h at room temperature. The mixture was quenched by cautious addition of 5% aqueous citric acid (20 ml) then diluted with brine (30 ml) and extracted with EtOAc (2×100 ml). The combined organic extracts were dried over anhydrous magnesium sulfate, filtered and evaporated under reduced pressure to give a white solid (5.2 g). Purification by Biotage™ chromatography (90 g, Si) eluting with cyclohexane:EtOAc (3:1) gave the title compound (2.00 g) as a white solid.

Mass spectrum: Found: MH+ 429 H.p.l.c. Rt 3.38 min

Intermediate 13

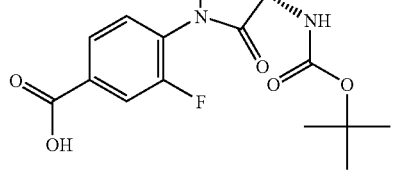

4-[(3S)-3-({[(1,1-Dimethylethyl)oxy]carbonyl}amino-2-oxo-1-pyrrolidinyl]-3-fluorobenzoic acid A solution of Intermediate 12 (0.59) in ethanol (15 ml) was added cautiously to palladium/carbon (Degussa type E101NE/W) (0.05 g) in a flask which had been pre-purged with nitrogen. The mixture was then stirred in an atmosphere of hydrogen for 6 h after which time the mixture was purged with nitrogen and cautiously filtered through filter agent (Celite 545) washing the filter pad with ethanol. The filtrate was concentrated under reduced pressure to give the title compound (0.396 g) as a grey solid.

Mass spectrum: Found: MH+ 339

Intermediate 14

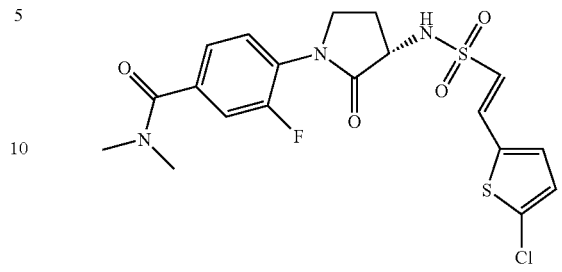

4-[(3S)-3-({[(E)-2-(5-Chloro-2-thienyl)ethenyl]sulfonyl}amino)-2-oxo-1-pyrrolidinyl]-3-fluoro-N,N-dimethylbenzamide The title compound was prepared from Intermediate 7 and (E)-2-(5-chloro-2-thienyl)ethenesulfonyl chloride using the synthetic procedure described for Intermediate 8.

Mass spectrum: Found: MH− 470 H.p.l.c. Rt 2.89 min

Example 1

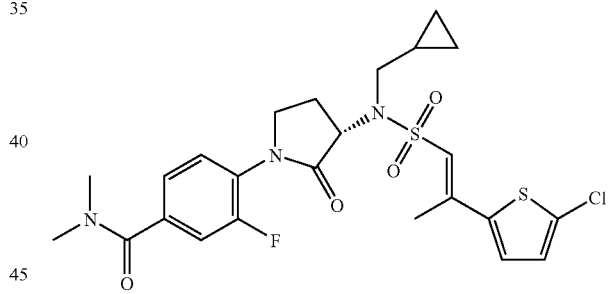

4-{(3S)-3-[{[(1E)-2-(5-Chloro-2-thienyl)-1-propen-1-yl]sulfonyl}(cycloprotylmethyl)amino]-2-oxo-1-pyrrolidinyl}-3-fluoro-N,N-dimethylbenzamide To a reaction vessel (altech tube) containing DCM (1 ml) was added Intermediate 8 ($6.1 \times 10^{-5}$ mole), cyclopropylmethanol ($6.1 \times 10^{-5}$ mole) and PS-triphenylphosphine (40 mg, 1.6 mmol/g). After shaking the reaction mixture for 5 min., bis(1,1-dimethylethyl) (E)-1,2-diazenedicarboxylate ($6.1 \times 10^{-5}$ mole) was added. The reaction was then shaken at room temperature for 16 h. Up to 3 additional equivalents of reagents were added to drive the reaction to completion. The reaction mixture was filtered, evaporated and then purified by mass-directed autoprep then Strata Phenyl SPE, to give the title compound (0.0162 g) as a clear gum.

Mass spectrum: Found: MH+ 540 H.p.l.c. Rt 3.36 min.

Using similar chemistry, the following compounds were prepared:

Example 2

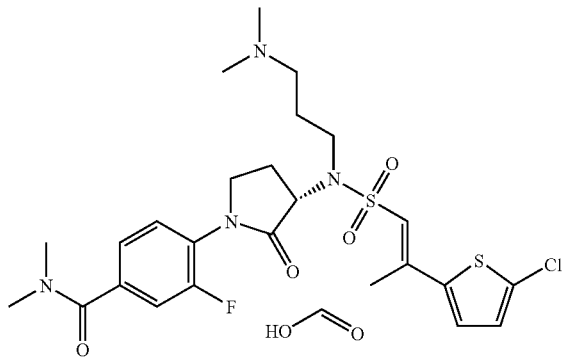

4-((3S)-3-{{[(1E)-2-(5-Chloro-2-thienyl)-1-propen-1-yl]sulfonyl}[3-(dimethylamino)propyl]amino}-2-oxo-1-Pyrrolidinyl)-3-fluoro-N,N-dimethylbenzamide formate (i.e. Formic acid 4-((3S)-3-{{[(1E)-2-(5-Chloro-2-thienyl)-1-propen-1-yl]sulfonyl}[3-(dimethylamino)propyl]amino}-2-oxo-1-pyrrolidinyl)-3-fluoro-N,N-dimethylbenzamide)

The reaction was carried out in DCM and the product purified by mass-directed autoprep.
Mass spectrum: Found: MH$^+$ 571 H.p.l.c. Rt 2.44 min.

Example 3

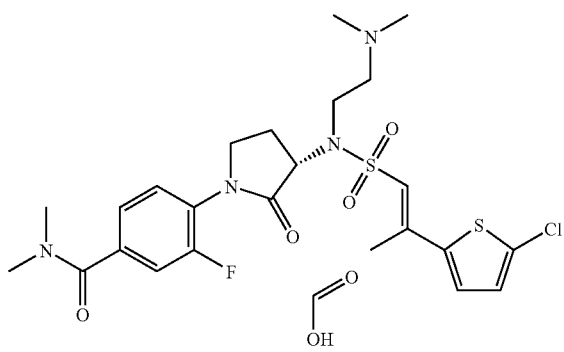

4-((3S)-3-{{[(1E)-2-(5-Chloro-2-thienyl)-1-propen-1-yl]sulfonyl}[2-(dimethylamino)ethyl]amino}-2-oxo-1-pyrrolidinyl)-3-fluoro-N,N-dimethylbenzamide formate The reaction was carried out in THF and then purified by preparative HPLC followed by Strata Phenyl SPE.
Mass spectrum: Found: MH$^+$ 557 H.p.l.c. Rt 2.41 min.

Example 4

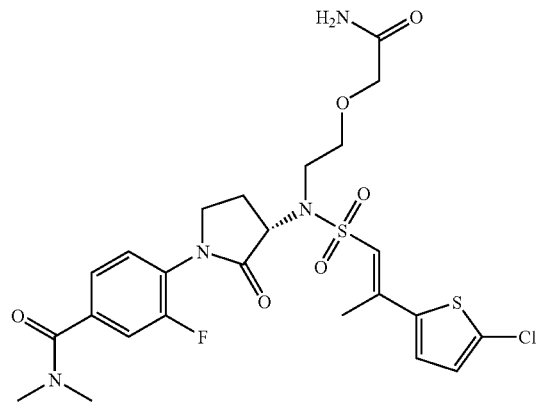

4-[(3S)-3-({2-[(2-Amino-2-oxoethyl)oxy]ethyl}{[(1E)-2-(5-chloro-2-thienyl)-1-propen-1-yl]sulfonyl}amino)-2-oxo-1-pyrrolidinyl]-3-fluoro-N,N-dimethylbenzamide The reaction was carried out in THF and then purified as described in Example 3.
Mass spectrum: Found: MH$^+$ 587 H.p.l.c. Rt 2.85 min

Example 5

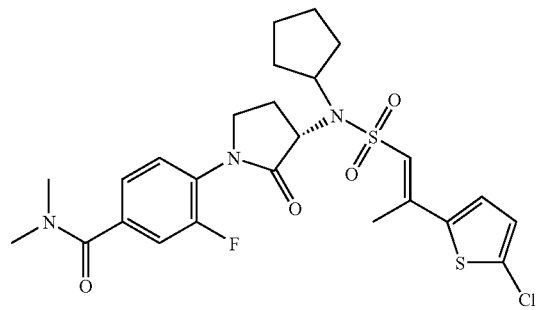

4-{(3S)-3-[{[(1E)-2-(5-Chloro-2-thienyl)-1-propen-1-yl]sulfonyl}(cyclopentyl)amino]-2-oxo-1-pyrrolidinyl}-3-fluoro-N,N-dimethylbenzamide The reaction was carried out in DCM and then purified as described In Example 3.
Mass spectrum: Found: MH$^+$ 554 H.p.l.c. Rt 3.46 min

Example 6

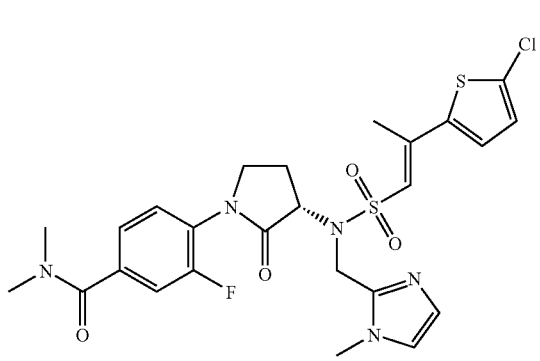

4-((3S)-3{{[(1E)-2-(5-Chloro-2-thienyl)-1-propen-1-yl]sulfonyl}[(1-methyl-1H-imidazol-2-yl)methyl]amino}-2-oxo-1-pyrrolidinyl)-3-fluoro-N,N-dimethylbenzamide The reaction was carried out in THF and then purified as described in Example 3.

Mass spectrum: Found: MH$^+$ 580 H.p.l.c. Rt 2.49 min

Example 7

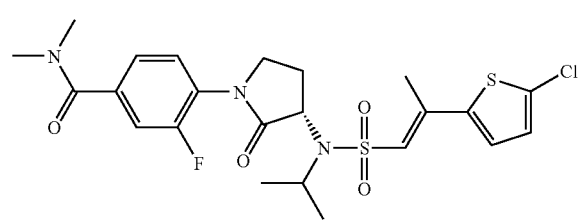

4-{(3S)-3-[{[(1E)-2-(5-Chloro-2-thienyl)-1-propen-1-yl]sulfonyl}(1-methylethyl)amino]-2-oxo-1-pyrrolidinyl}-3-fluoro-N,N-dimethylbenzamide The reaction was carried out in THF and then purified as described in Example 3.

Mass spectrum: Found: MH$^+$ 528 H.p.l.c. Rt 3.32 min

Example 8

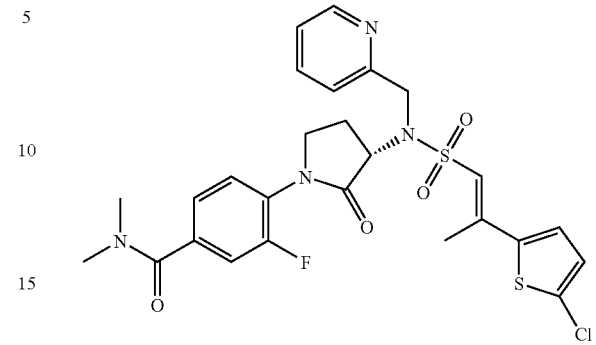

4-{(3S)-3-[{[(1E)-2-(5-Chloro-2-thienyl)-1-propen-1-yl]sulfonyl}(2-pyridinylmethyl)amino]-2-oxo-1-pyrrolidinyl}-3-fluoro-N,N-dimethylbenzamide The reaction was carried out in THF and then purified as described in Example 3.

Mass spectrum: Found: MH$^+$ 577 H.p.l.c. Rt 3.13 min

Example 9

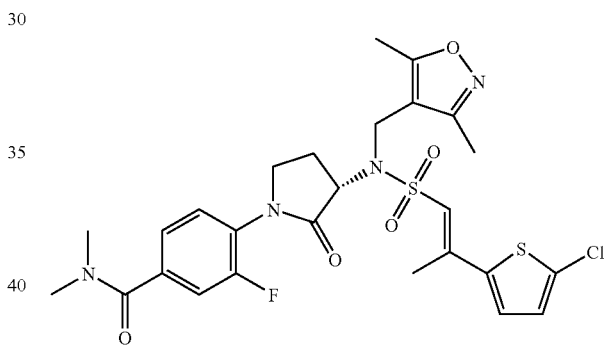

4-((3S)-3-{{[(1E)-2-(5-Chloro-2-thienyl)-1-propen-1-yl]sulfonyl}[(3,5-dimethyl-4-isoxazolyl)methyl]amino}-2-oxo-1-pyrrolidinyl)-3-fluoro-N,N-dimethylbenzamide The reaction was carried out in THF and then purified as described in Example 1.

Mass spectrum: Found: MH$^+$ 595 H.p.l.c. Rt 3.23 min

Example 10

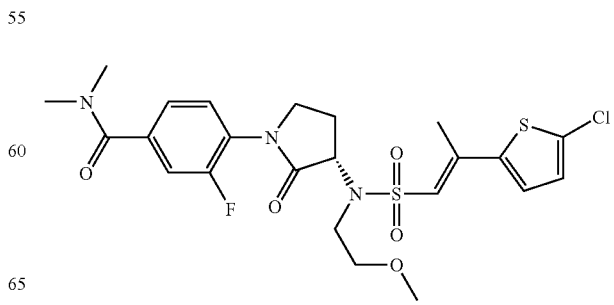

4-((3S)-3-{{[(1E)-2-(5-Chloro-2-thienyl)-1-propen-1-yl]sulfonyl}[2-(methyloxy)ethyl]amino}-2-oxo-1-pyrrolidinyl)-3-fluoro-N,N-dimethylbenzamide The reaction was carried out in THF and then purified as described in Example 3.

Mass spectrum: Found: MH+ 544 H.p.l.c. Rt 3.20 min

Example 11

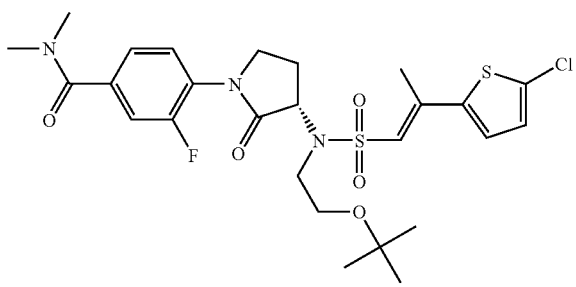

4-[(3S)-3-({[(1E)-2-(5-Chloro-2-thienyl)-1-propen-1-yl]sulfonyl}{2-[(1,1-dimethylethyl)oxy]ethyl}amino)-2-oxo-1-pyrrolidinyl]-3-fluoro-N,N-dimethylbenzamide The reaction was carried out in THF and then purified as described in Example 3.

Mass spectrum: Found: MH+ 586 H.p.l.c. Rt 3.51 min

Example 12

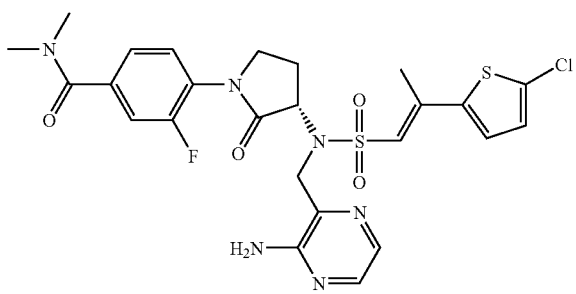

4-[(3S)-3-([(3-Amino-2-pyrazinyl)methyl]{[(1E)-2-(5-chloro-2-thienyl)-1-propen-1-yl]sulfonyl}amino)-2-oxo-1-pyrrolidinyl]-3-fluoro-N,N-dimethylbenzamide The reaction was carried out in THF and then purified as described in Example 3.

Mass spectrum: Found: MH+ 593 H.p.l.c. Rt 3.04 min

Example 13

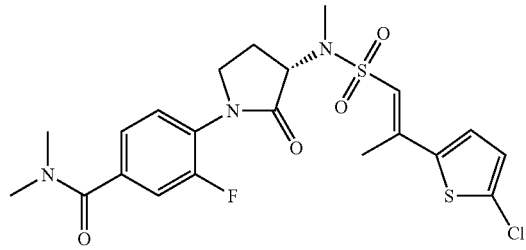

4-{(3S)-3-[{[(1E)-2-(5-Chloro-2-thienyl)-1-propen-1-yl]sulfonyl}(methyl)amino]-2-oxo-1-pyrrolidinyl}-3-fluoro-N,N-dimethylbenzamide A mixture of Intermediate 8 (0.047 g), N,N-di-tert-butyl azodicarboxylate (0.033 g) and triphenylphosphine (0.038 g) in dry THF (1 ml) was stirred at room temperature for 5 min. Anhydrous methanol (0.035 ml) was added and the mixture was stirred at room temperature for 63 h and then evaporated in vacuo. The resultant crude product was purified by mass directed preparative h.p.l.c. and appropriate fractions were combined and evaporated in vacuo to remove most organic solvent. The resultant aqueous solution was freeze-dried to give the title compound as a fluffy white solid (0.037 g).

Mass spectrum: Found: MH+ 500 H.p.l.c. Rt 3.13 min
$^1$H-NMR δ (CDCl$_3$) 2.27-2.40 (m, 1H), 2.50 (d, 3H), 2.51-2.61 (m, 1H), 2.91 (s, 3H), 3.01 (s, 3H), 3.11 (s, 3H), 3.71-3.79 (m, 1H), 3.83-3.92 (m, 1H), 5.00 (dd, 1H), 6.85 (d, 1H), 6.90 (broad s, 1H), 7.12 (d, 1H), 7.23-7.28 (m, 2H), 7.46 (t, 1H).

Example 14

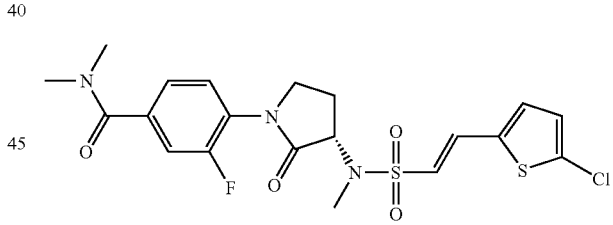

4-{(3S)-3-[{[(E)-2-(5-chloro-2-thienyl)ethenyl]sulfonyl}(methyl)amino]-2-oxo-1-pyrrolidinyl}-3-fluoro-N,N-dimethylbenzamide A solution of Intermediate 14 (0.0289) in dry DMF (3 ml) was treated with potassium carbonate (0.050 g) and methyl iodide (0.025 g) and stirred at 40° C. in a reactivial for 4 h. Solvent was removed under reduced pressure, partitioning the residue between chloroform and saturated aqueous sodium bicarbonate. The separated organic layer was passed through a hydrophobic frit and concentrated under reduced pressure to provide crude product which was purified via mass directed preparative h.p.l.c. to give title compound (0.015 g) as a white powder.

Mass spectrum: Found: MNH$_4$+ 505 H.p.l.c. Rt 3.04 min
$^1$H NMR (MeOD): 2.38 (m, 1H), 2.52 (m, 1H), 2.82 (s, 3H), 3.00 (s, 3H), 3.09 (s, 3H), 3.76 (broad t, 1H), 3.90 (m, 1H), 4.98 (broad t, 1H In Vitro Assay for Inhibition of Factor Xa Compounds of the present invention were tested for their Factor Xa inhibitory activity as determined in vitro by their ability to Inhibit human Factor Xa in a fluorogenic assay, using Rhodamine 110, bis-CBZ-glycylglycyl-L-arginine amide as the fluorogenic substrate. Compounds were diluted from a 10 mM stock solution in dimethylsulfoxide at appropriate concentrations. Assay was performed at room temperature using buffer consisting of: 50 mM Tris-HCl, 150 mM NaCl, 5 mM $CaCl_2$, pH 7.4. containing human Factor Xa (final conc. Of 0.0003U.ml-1). Compound and enzyme were preincubated for 15 min prior to addition of the substrate (final conc. of 10 μM). The reaction was stopped after 3 hrs with the addition of H-D-Phe-Pro-Arg-Chloromethylketone. An LJL-Analyst fluorimeter was used to monitor fluorescence with 485 nm excitation/535 nm emission. To obtain $IC_{50}$ values the data were analysed using ActivityBase® and XLfit®.

Calculation of Ki values:

$$Ki=IC_{50}/(1+[Substrate]/Km)$$

The Ki value for the above assay can be obtained by dividing the $IC_{50}$ value by 1.6.

All of the synthetic Example compounds tested by the above described In vitro assay were found to exhibit Factor Xa inhibitory activity. Preferably, compounds have a Ki value of less than 0.1 μM (Examples 1, 2, 3, 4, 5, 6, 7, 8, 9, 10, 11, 12, 13, 14). More preferably, compounds have a Ki value of less than 100 nM (Examples 1, 2, 3, 4, 5, 6, 7, 8, 9, 10, 11, 12, 13, 14). Most preferably, compounds have a Ki value of less than 10 nM (Examples 1, 2, 4, 5, 6, 7, 8, 9, 10, 11, 12, 13, 14).

Method for Measurement of Prothrombin Time (PT)

Blood was collected into a sodium citrate solution (ratio 9:1) to give a final concentration of 0.38% citrate. Plasma was generated by centrifugation of citrated blood samples at 1200×g for 20 min at 4° C. and stored at −20° C. until use. PT analysis was conducted using plasma pooled from 4 separate donors (2 male and 2 female).

The PT test was performed using the BCS Coagulation Analyzer (Dade Behring). For assay, 50 ul of plasma containing test compound at concentrations ranging from 0.03 to 100 uM (made from a 100 uM stock containing 1% DMSO in plasma) was combined with 100 ul of Thromboptastin C Plus (Dade Behring). Upon addition of the reagents, absorbance at 405 nm was monitored and time to clot formation is determined (normal range for human plasma is 10.6-12.4 seconds).

All of the synthetic Example compounds tested by the above described assay were found to exhibit activity.

General Purification and Analytical Methods

LC/MS Method

Analytical HPLC was conducted on a Supelcosil LCABZ+PLUS column (3 μm, 3.3 cm×4.6 mm ID) eluting with 0.1% $HCO_2H$ and 0.01 M ammonium acetate in water (solvent A), and 95% acetonitrile and 0.05% $HCO_2H$ in water (solvent B), using the following elution gradient 0-0.7 minutes 0% B, 0.7-4.2 minutes 0→100% B, 4.2-5.3 minutes 100% B, 5.3-5.5 minutes 100→0% B at a flow rate of 3 ml/minutes (System 1). The mass spectra (MS) were recorded on a Fisons VG Platform mass spectrometer using electrospray positive ionisation [(ES+ve to give $MH^+$ and $M(NH_4)^+$ molecular ions] or electrospray negative ionisation [(ES−ve to give $(M-H)^-$ molecular ion] modes.

$^1H$ nmr spectra were recorded using a Bruker DPX 400 MHz spectrometer using tetramethylsilane as the external standard.

Biotage™ chromatography refers to purification carried out using equipment sold by Dyax Corporation (either the Flash 40i or Flash 150i) and cartridges pre-packed with KPSil.

Mass directed autoprep refers to methods where the material was purified by high performance liquid chromatography on a HPLCABZ+ 5 μm column (5 cm×10 mm i.d.) with 0.1% $HCO_2H$ in water and 95% MeCN, 5% water (0.5% $HCO_2H$) utilising the following gradient elution conditions: 0-1.0 minutes 5% B, 1.0-8.0 minutes 5→30% B, 8.0-8.9 minutes 30% B, 8.9-9.0 minutes 30→95% B, 9.0-9.9 minutes 95% B, 9.9-10 minutes 95→0% B at a flow rate of 8 ml $minutes^{-1}$ (System 2). The Gilson 202-fraction collector was triggered by a VG Platform Mass Spectrometer on detecting the mass of interest.

Preparative h.p.l.c. refers to methods where the material was purified by high performance liquid chromatography on a HPLCABZ+ 5 μm column (10 cm×21.2 mm i.d.) with 0.1% $HCO_2H$ in water (A) and MeCN (0.5% $HCO_2H$) (B) utilising the generic gradient elution conditions expressed as "x to y" gradient with a gradient system as follows: 0-1.45 minutes x % B, 1.45-20 minutes x→y % B, 20-24 minutes y→95% B, 24-30 minutes 95% B, 32-34 minutes 95→x % B at a flow rate of 8 ml $minutes^{-1}$. The Gilson 233 fraction collector was triggered by UV (254 nm).

SPE (solid phase extraction) refers to the use of cartridges sold by International Sorbent Technology Ltd.

Strata Phenyl SPE refers to the use of cartridges sold by Phenomenex. The compound was loaded onto a cartridge previously conditioned with MeCN and equilibrated with 5% MeCN in water. The compound was eluted with 0.1% $HCO_2H$ in water and MeCN (0.5% $HCO_2H$) in a suitable gradient on a Combiflash Optix 10.

What is claimed is:

1. A compound of formula (I):

wherein:

$R^1$ represents a group selected from:

each ring of which optionally includes a further heteroatom N,

Z represents an optional substituent halogen, alk represents alkylene or alkenylene, T represents S, O or NH;

$R^2$ represents —$C_{1-6}$alkyl, —$C_{1-3}$alkylCN, —$C_{0-3}$alkylR$^c$, —$C_{1-3}$alkylR$^f$, —$C_{2-3}$alkylNR$^a$R$^b$, —$C_{2-3}$alkylOC$_{1-6}$alkyl, —$C_{2-3}$alkylOC$_{1-3}$alkylCONR$^a$R$^b$, with the proviso that $R^2$ does not represent $C_{2-3}$alkylmorpholino;

$R^a$ and $R^b$ independently represent hydrogen, or —$C_{1-6}$alkyl;

$R^c$ represents —$C_{3-6}$cycloalkyl;

$R^f$ represents phenyl or a 5- or 6-membered aromatic heterocyclic ring, containing at least one heteroatom selected from O, N(O)$_m$ or S(O)$_n$, optionally substituted by 0 to 2 groups selected from —$C_{1-4}$alkyl or —NH$_2$;

n represents 0-2;

m represents 0 or 1;

X represents phenyl or a 5- or 6-membered aromatic heterocyclic group containing at least one heteroatom selected from O, N or S, each of which is optionally substituted by 0-2 groups selected from: halogen, —$C_{1-4}$ alkyl, —$C_{2-4}$alkenyl, —CN, —CF$_3$, —NR$^a$R$^b$, —$C_{0-4}$ alkylOR$^e$, —C(O)R$^d$ and —C(O)NR$^a$R$^b$;

$R^e$ represents hydrogen or —$C_{1-6}$alkyl;

Y represents a substituent selected from hydrogen, halogen, —$C_{1-4}$alkyl, —$C_{2-4}$alkenyl, —NR$^a$R$^b$, —NO$_2$, —C(O)NR$^a$R$^b$, —N(C$_{1-4}$alkyl)(CHO), —NHCOC$_{1-4}$ alkyl, —NHSO$_2$R$^d$, —$C_{0-4}$alkylOR$^e$, —C(O)R$^d$, —S(O)$_n$R$^d$, or —S(O)$_2$NR$^a$R$^b$;

$R^d$ represents —$C_{1-6}$alkyl;

or a pharmaceutically acceptable salt or solvate thereof.

2. A compound according to claim 1 wherein $R^1$ represents a group selected from:

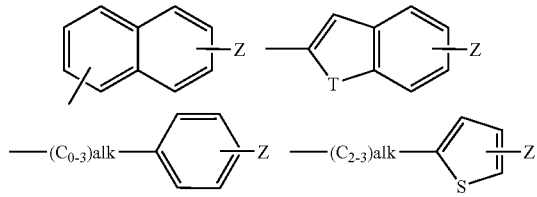

each ring of which optionally contains a further heteroatom N,

Z represents an optional substituent halogen, alk represents alkylene or alkenylene, and T represents S, O or NH.

3. A compound according to claim 1 wherein $R^2$ represents —$C_{1-6}$alkyl, —$C_{0-3}$alkylR$^c$, $C_{1-3}$alkylR$^f$; —$C_{2-3}$alkylNR$^a$R$^b$, —$C_{2-3}$alkylOC$_{1-6}$alkyl, or —$C_{2-3}$alkylOC$_{1-3}$alkylCONR$^a$R$^b$.

4. A compound according to claim 1 wherein X represents phenyl or a 5 or 6 membered aromatic heterocyclic group consisting of at least one heteroatom selected from O, N or S, each of which is optionally substituted by 0-2 groups selected from: halogen, —$C_{1-4}$alkyl or —NR$^a$R$^b$.

5. A compound according to claim 1 wherein Y represents a substituent selected from —C(O)NR$^a$R$^b$, —S(O)$_n$R$^d$, —S(O)$_2$NR$^a$R$^b$, —N(C$_{1-4}$alkyl)(CHO) or —NHSO$_2$R$^d$.

6. A compound selected from:

4-{(3S)-3-[{[(1E)-2-(5-Chloro-2-thienyl)-1-propen-1-yl]sulfonyl}(cyclopropylmethyl)amino]-2-oxo-1-pyrrolidinyl}-3-fluoro-N,N-dimethylbenzamide;

4-((3S)-3-{{[(1E)-2-(5-Chloro-2-thienyl)-1-propen-1-yl]sulfonyl}[3-(dimethylamino)propyl]amino}-2-oxo-1-pyrrolidinyl)-3-fluoro-N,N-dimethylbenzamide;

4-((3S)-3-{{[(1E)-2-(5-Chloro-2-thienyl)-1-propen-1-yl]sulfonyl}[2-(dimethylamino)ethyl]amino}-2-oxo-1-pyrrolidinyl)-3-fluoro-N,N-dimethylbenzamide;

4-[(3S)-3-({2-[(2-Amino-2-oxoethyl)oxy]ethyl}{[(1E)-2-(5-chloro-2-thienyl)-1-propen-1-yl]sulfonyl}amino)-2-oxo-1-pyrrolidinyl]-3-fluoro-N,N-dimethylbenzamide;

4-{(3S)-3-[{[(1E)-2-(5-Chloro-2-thienyl)-1-propen-1-yl]sulfonyl}(cyclopentyl)amino]-2-oxo-1-pyrrolidinyl}-3-fluoro-N,N-dimethylbenzamide;

4-((3S)-3-{{[(1E)-2-(5-Chloro-2-thienyl)-1-propen-1-yl]sulfonyl}[(1-methyl-1H-imidazol-2-yl)methyl]amino}-2-oxo-1-pyrrolidinyl)-3-fluoro-N,N-dimethylbenzamide;

4-{(3S)-3-[{[(1E)-2-(5-Chloro-2-thienyl)-1-propen-1-yl]sulfonyl}(1-methylethyl)amino]-2-oxo-1-pyrrolidinyl}-3-fluoro-N,N-dimethylbenzamide;

4-{(3S)-3-[{[(1E)-2-(5-Chloro-2-thienyl)-1-propen-1-yl]sulfonyl}(2-pyridinylmethyl)amino]-2-oxo-1-pyrrolidinyl}-3-fluoro-N,N-dimethylbenzamide;

4-((3S)-3-{{[(1E)-2-(5-Chloro-2-thienyl)-1-propen-1-yl]sulfonyl}[(3,5-dimethyl-4-isoxazolyl)methyl]amino}-2-oxo-1-pyrrolidinyl)3-fluoro-N,N-dimethylbenzamide;

4-((3S)-3{{[(1E)-2-(5-Chloro-2-thienyl)-1-propen-1-yl]sulfonyl}[2-(methyloxy)ethyl]amino}-2-oxo-1-pyrrolidinyl)-3-fluoro-N,N-dimethylbenzamide;

4-[(3S)-3-({[(1E)-2-(5-Chloro-2-thienyl)-1-propen-1-yl]sulfonyl}{2-[(1,1-dimethylethyl)oxy]ethyl}amino)-2-oxo-1-pyrrolidinyl]-3-fluoro-N,N-dimethylbenzamide;

4-[(3S)-3-([(3-Amino-2-pyrazinyl)methyl]{[(1E)-2-(5-chloro-2-thienyl)-1-propen-1-yl]sulfonyl}amino)-2-oxo-1-pyrrolidinyl]-3-fluoro-N,N-dimethylbenzamide;

4-{(3S)-3-[{[(1E)-2-(5-Chloro-2-thienyl)-1-propen-1-yl]sulfonyl}(methyl)amino]-2-oxo-1-pyrrolidinyl}-3-fluoro-N,N-dimethylbenzamide; and 4-{(3S)-3-[{[(E)-2-(5-chloro-2-thienyl)ethenyl]sulfonyl}(methyl)amino]-2-oxo-1-pyrrolidinyl}-3-fluoro-N,N-dimethylbenzamide;

or pharmaceutically acceptable salt or solvate thereof.

7. A pharmaceutical composition comprising a compound according to claim 1 together with at least one pharmaceutical carrier or excipient.

8. A process for preparing a compound of formula (I) which comprises reacting a compound of formula (II) with a compound of formula (III):

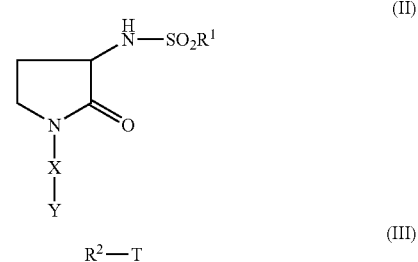

where $R^2$ is —$C_{1-6}$alkyl, —$C_{1-3}$alkylCN, —$C_{0-3}$alkylR$^c$, —$C_{1-3}$alkylR$^f$, —$C_{2-3}$alkylNR$^a$R$^b$, —$C_{2-3}$alkylOC$_{1-6}$alkyl, —$C_{2-3}$alkylOC$_{1-3}$alkylCONR$^a$R$^b$, with the proviso that $R^2$ does not represent $C_{2-3}$alkylmorpholino, and T is a suitable leaving group.

* * * * *